United States Patent
Segal et al.

(10) Patent No.: US 7,601,172 B2
(45) Date of Patent: *Oct. 13, 2009

(54) MECHANICAL APPARATUS AND METHOD FOR ARTIFICIAL DISC REPLACEMENT

(75) Inventors: Jerome Segal, Rockville, MD (US); Matthew Thomas Yurek, San Diego, CA (US); Hansen A. Yuan, Syracuse, NY (US); Anthony Tung Yeung, Phoenix, AZ (US)

(73) Assignee: Ouroboros Medical, Inc., Pleasanton, CA (US)

( * ) Notice: Subject to any disclaimer, the term of this patent is extended or adjusted under 35 U.S.C. 154(b) by 768 days.

This patent is subject to a terminal disclaimer.

(21) Appl. No.: 11/273,299

(22) Filed: Nov. 14, 2005

(65) Prior Publication Data

US 2006/0287729 A1    Dec. 21, 2006

Related U.S. Application Data

(63) Continuation-in-part of application No. 11/153,776, filed on Jun. 15, 2005, and a continuation-in-part of application No. 11/173,034, filed on Jul. 1, 2005, now Pat. No. 7,442,210.

(51) Int. Cl.
*A61F 2/44* (2006.01)
(52) U.S. Cl. .............................. 623/17.11; 623/17.12
(58) Field of Classification Search ............... 606/246, 606/279; 623/17.11, 17.12, 17.16
See application file for complete search history.

(56) References Cited

U.S. PATENT DOCUMENTS

| 5,192,326 | A | 3/1993 | Bao et al. |
|---|---|---|---|
| 5,549,679 | A | 8/1996 | Kuslich |
| 5,562,736 | A | 10/1996 | Ray et al. |
| 5,571,189 | A | 11/1996 | Kuslich |
| 5,989,252 | A | 11/1999 | Fumex |
| 6,224,630 | B1 | 5/2001 | Bao et al. |
| 6,245,107 | B1 * | 6/2001 | Ferree .................. 606/279 |
| 6,332,894 | B1 | 12/2001 | Stalcup et al. |
| 6,371,990 | B1 | 4/2002 | Ferree |
| 6,419,704 | B1 | 7/2002 | Ferree |
| 6,425,919 | B1 | 7/2002 | Lambrecht |

(Continued)

*Primary Examiner*—Thomas C Barrett
*Assistant Examiner*—Andrew Yang
(74) *Attorney, Agent, or Firm*—Michael Klicpera

(57) ABSTRACT

The present invention relates to a device and method which may be used to reinforce the native annulus during spinal surgery. The device is a catheter based device which is placed into the inter-vertebral space following discectomy performed by either traditional surgical or endoscopic approaches. The distal end of the catheter is comprised of an expansile loop which may be increased in diameter by advancement of a portion of the catheter via its proximal end, such proximal end remaining external to the body. The expansile loop may be formed such that when the loop is diametrically contracted the loop feeds into its other end, similar to a snake eating its own tail. Stabilization of the outer portion of the loop and pulling out the inner portion will thereby increase the overall diameter of the loop while maintaining it as a closed loop or torus. The expansile loop then uses an attachment means to secure it to substantially healthy tissues of the annulus, nucleus, or endplates. The present invention comprises four embodiments and can be used to 1) facilitate disk fusing, 2) perform an artificial replacement of the nucleus, 3) perform an artificial replacement of the annulus, or 4, perform an artificial replacement of both the nucleus and annulus.

57 Claims, 14 Drawing Sheets

U.S. PATENT DOCUMENTS

| | | |
|---|---|---|
| 6,508,839 B1 | 1/2003 | Lambrecht et al. |
| 6,511,498 B1 | 1/2003 | Fumex |
| 6,592,625 B2 | 7/2003 | Cauthen |
| 6,685,695 B2 | 2/2004 | Ferree |
| 6,712,853 B2 | 3/2004 | Kuslich |
| 6,726,685 B2 | 4/2004 | To et al. |
| 6,733,496 B2 | 5/2004 | Sharkey |
| 6,733,533 B1 | 5/2004 | Lozier |
| 6,821,276 B2 | 11/2004 | Lambrecht et al. |
| 6,827,743 B2 | 12/2004 | Eisermann et al. |
| 6,830,589 B2 | 12/2004 | Erickson |
| 6,835,205 B2 | 12/2004 | Atkinson et al. |
| 6,883,520 B2 | 4/2005 | Lambrecht et al. |
| 6,969,404 B2 | 11/2005 | Ferree |
| 7,318,840 B2 | 1/2008 | McKay |
| 7,445,634 B2 * | 11/2008 | Trieu .................... 623/17.11 |
| 2002/0077701 A1 | 6/2002 | Kuslich |
| 2002/0189622 A1 | 12/2002 | Cauthen et al. |
| 2003/0040796 A1 | 2/2003 | Ferree |
| 2003/0074075 A1 | 4/2003 | Thomas et al. |
| 2003/0093155 A1 | 5/2003 | Lambrecht et al. |
| 2003/0120345 A1 | 6/2003 | Cauthen |
| 2003/0153976 A1 * | 8/2003 | Cauthen et al. .......... 623/17.16 |
| 2003/0158604 A1 | 8/2003 | Cauthen et al. |
| 2003/0163200 A1 | 8/2003 | Cauthen |
| 2003/0187507 A1 | 10/2003 | Cauthen |
| 2003/0187508 A1 | 10/2003 | Cauthen |
| 2003/0199979 A1 | 10/2003 | McGuckin |
| 2003/0220690 A1 | 11/2003 | Cauthen |
| 2003/0220693 A1 | 11/2003 | Cauthen |
| 2003/0220694 A1 | 11/2003 | Cauthen |
| 2004/0010317 A1 | 1/2004 | Lambrecht et al. |
| 2004/0073308 A1 | 4/2004 | Kuslich et al. |
| 2004/0097924 A1 | 5/2004 | Lambrecht et al. |
| 2004/0097980 A1 | 5/2004 | Ferree |
| 2004/0127992 A1 | 7/2004 | Serhan et al. |
| 2004/0143333 A1 | 7/2004 | Bain et al. |
| 2004/0186471 A1 | 9/2004 | Trieu |
| 2004/0260397 A1 | 12/2004 | Lambrecht et al. |
| 2004/0267368 A1 | 12/2004 | Kuslich |
| 2005/0049592 A1 | 3/2005 | Keith et al. |
| 2005/0069571 A1 | 3/2005 | Slivka et al. |
| 2005/0070913 A1 | 3/2005 | Milbocker et al. |
| 2005/0149191 A1 | 7/2005 | Cragg et al. |
| 2005/0149197 A1 | 7/2005 | Cauthen |
| 2005/0154463 A1 | 7/2005 | Trieu |
| 2007/0055265 A1 | 3/2007 | Schaller |
| 2007/0055272 A1 | 3/2007 | Schaller |
| 2007/0055273 A1 | 3/2007 | Schaller |
| 2007/0055275 A1 | 3/2007 | Schaller |
| 2007/0123986 A1 | 5/2007 | Schaller |

* cited by examiner

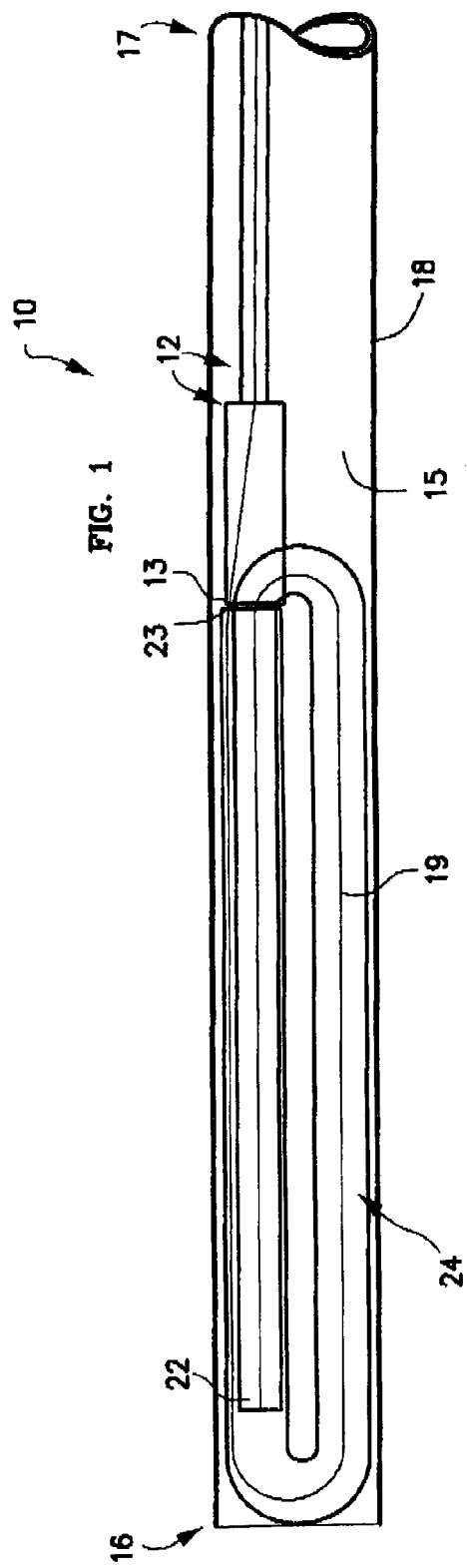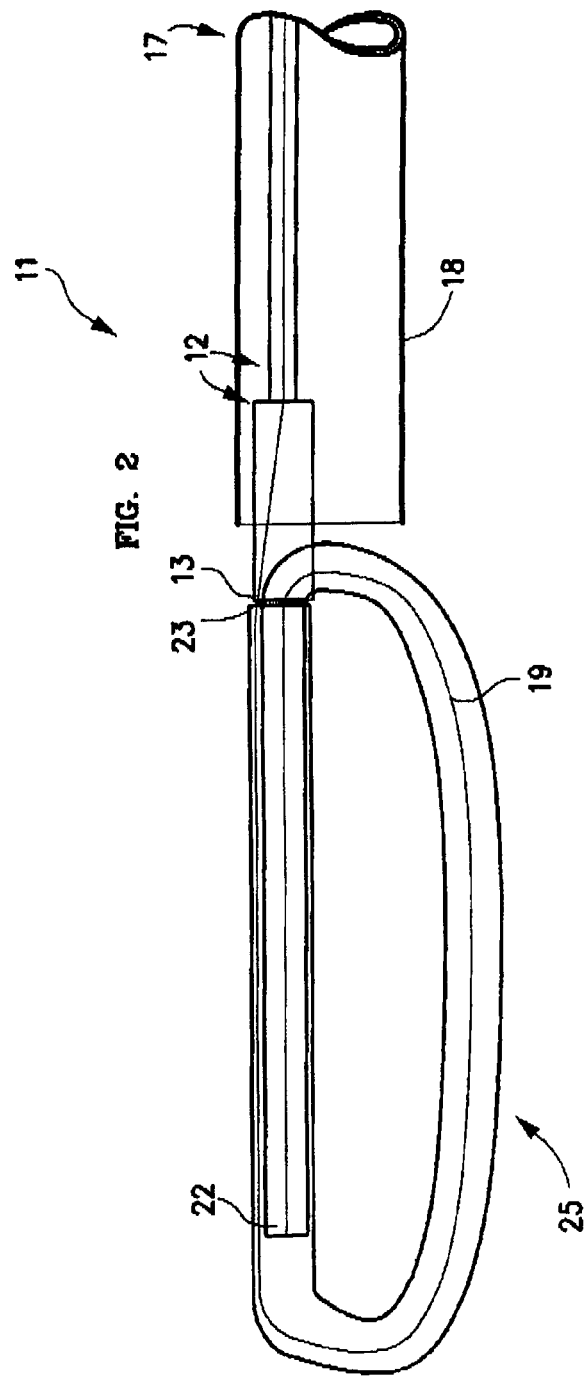

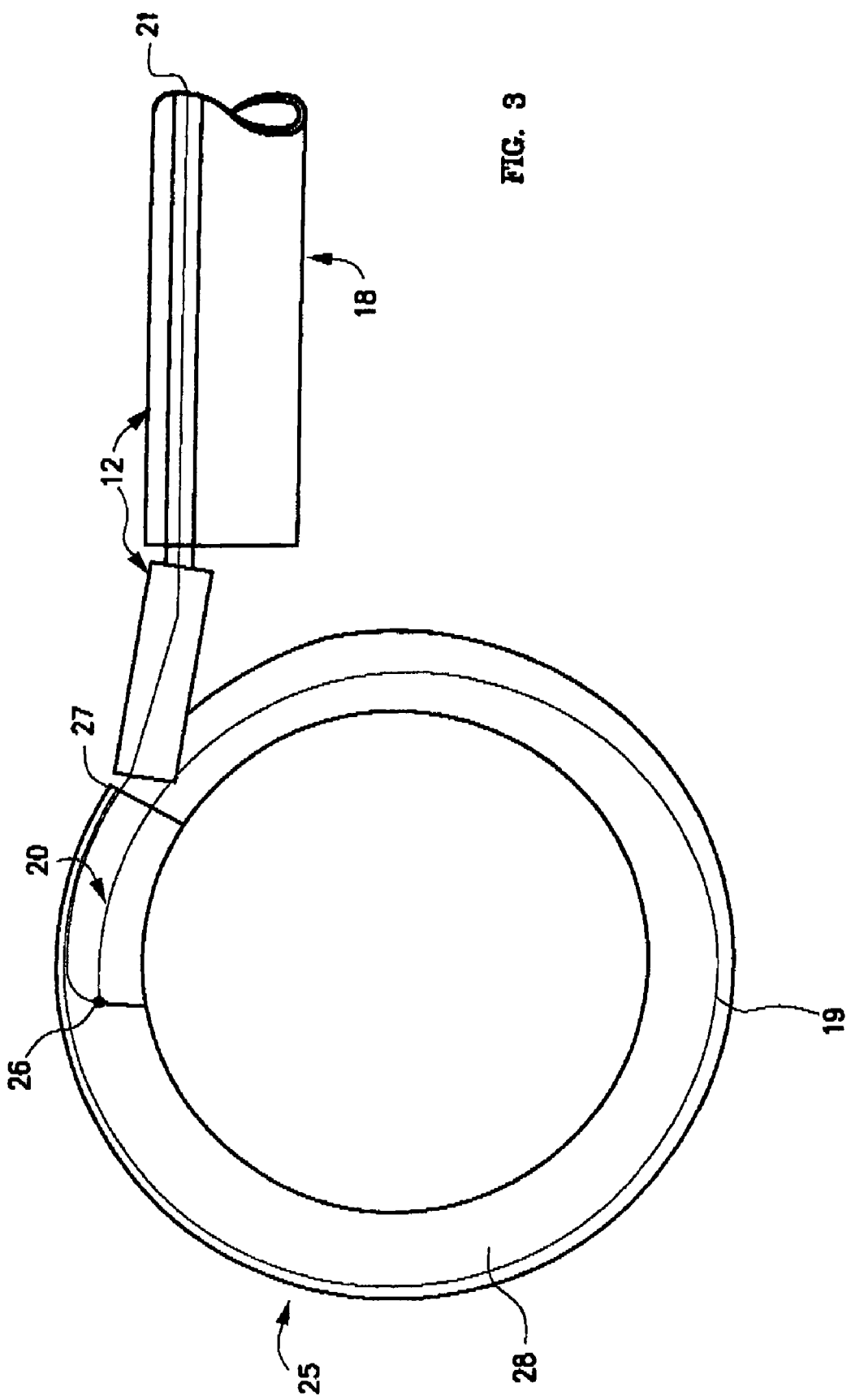

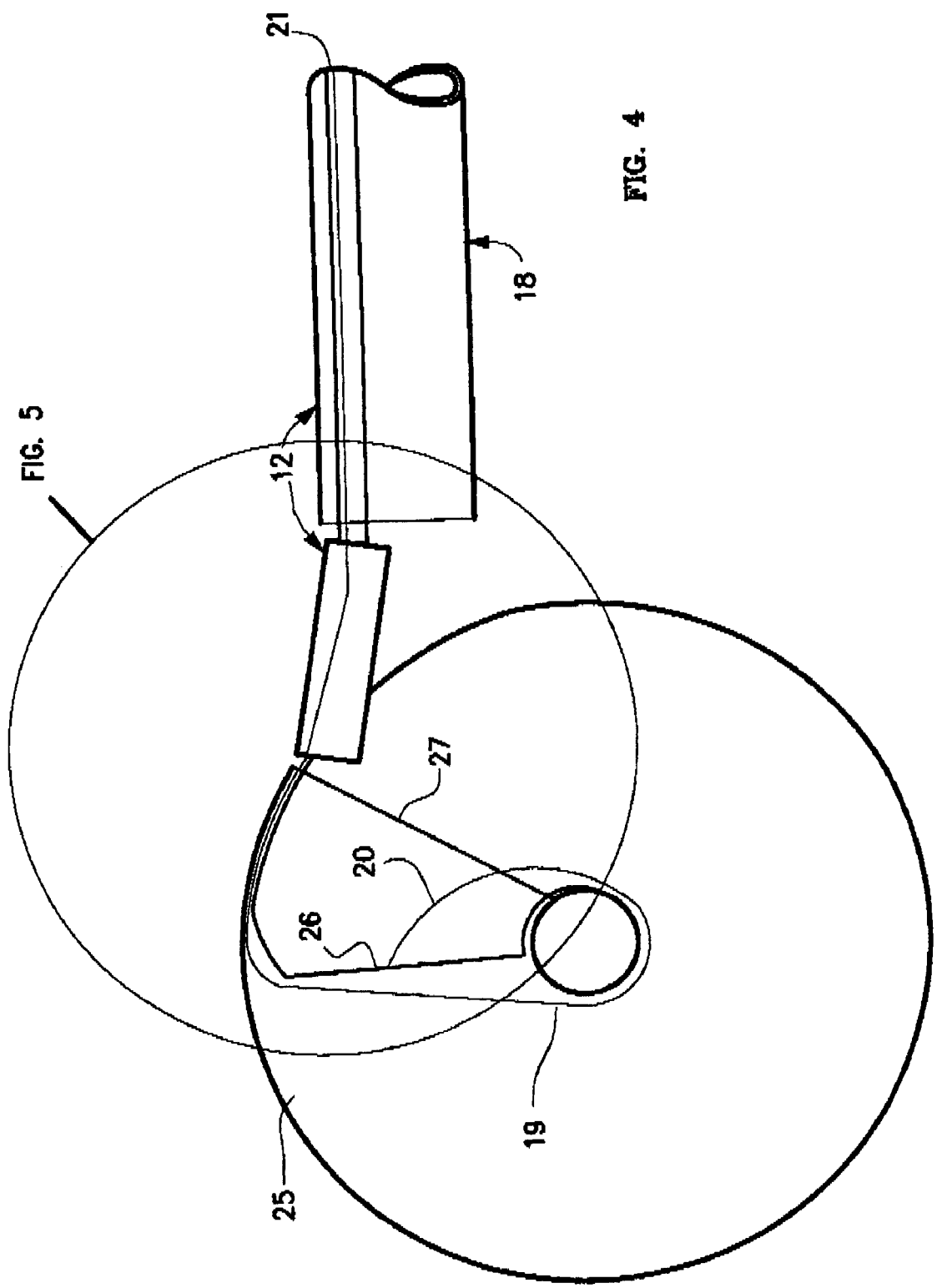

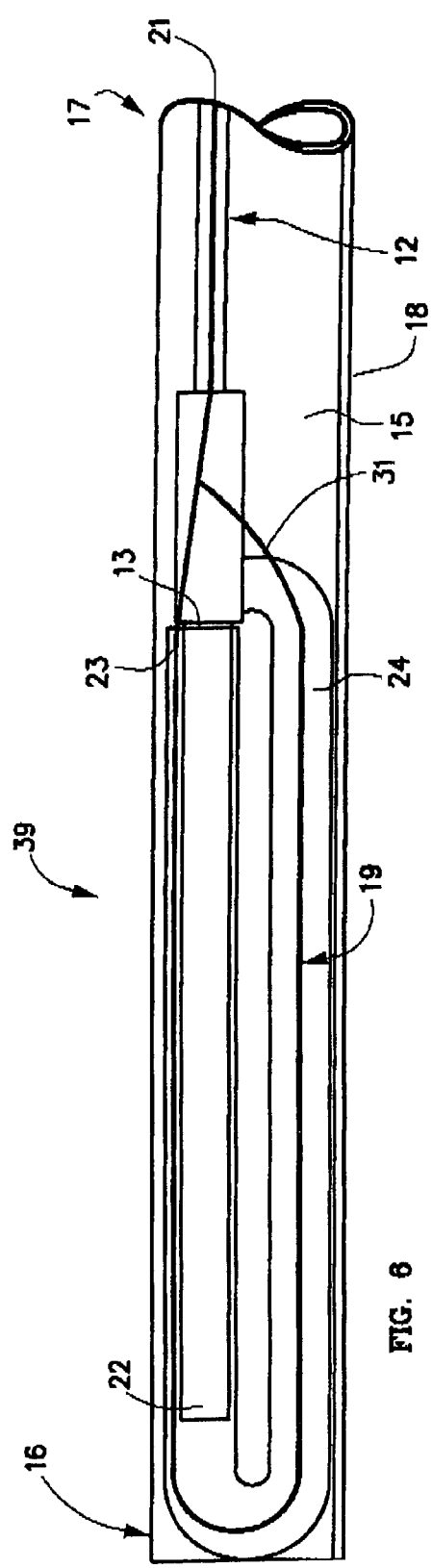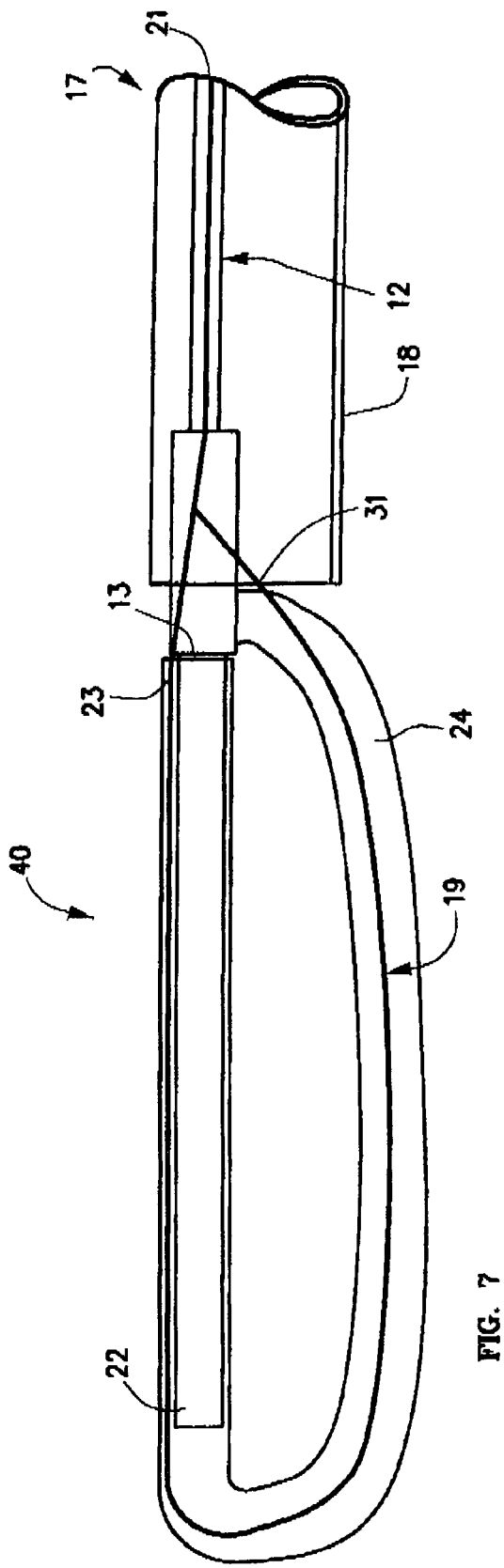

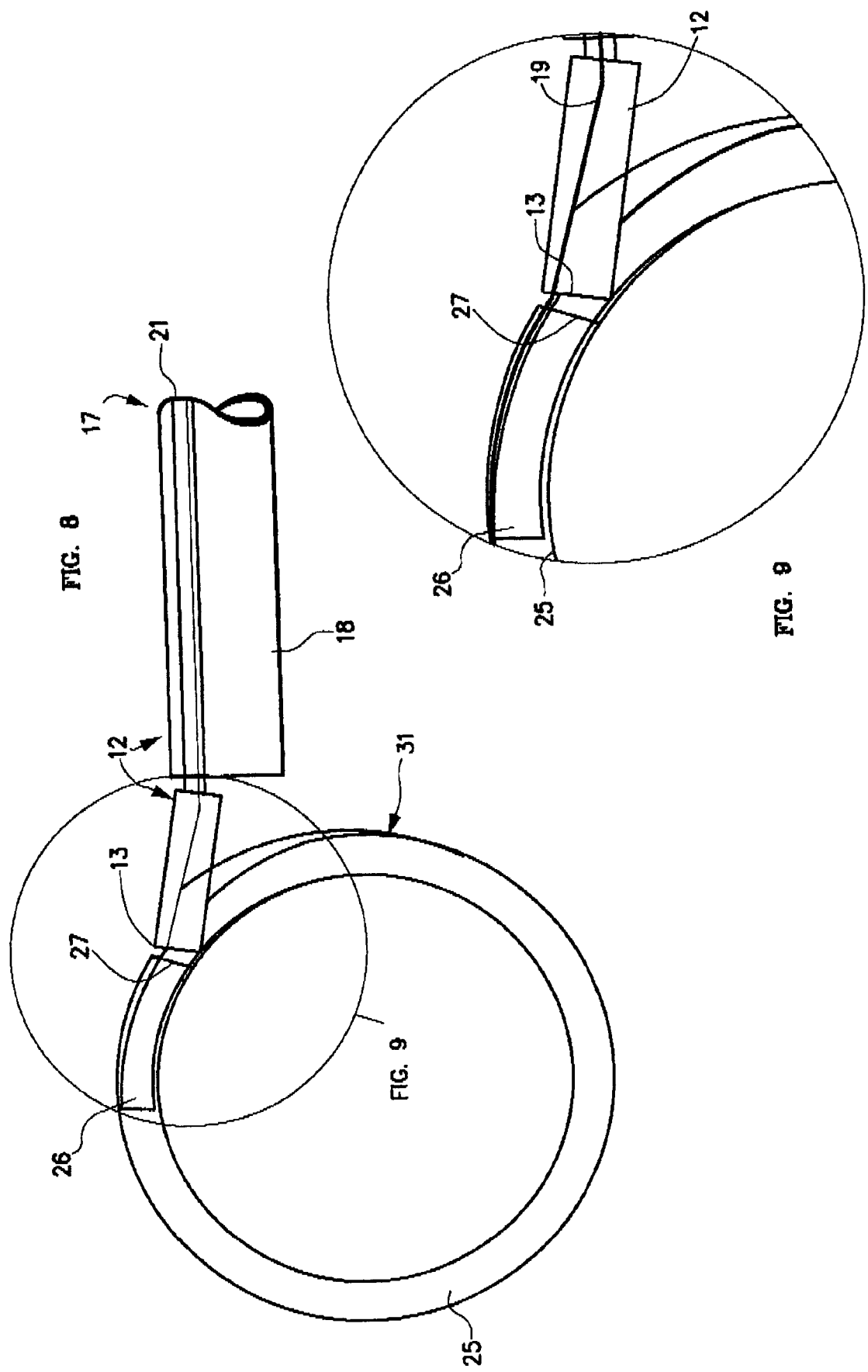

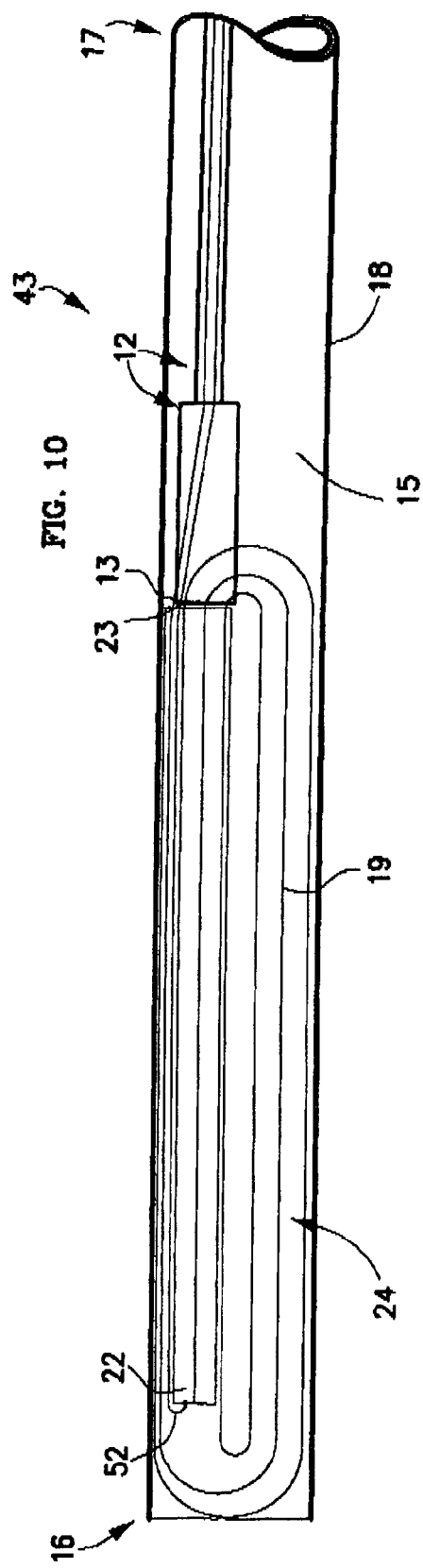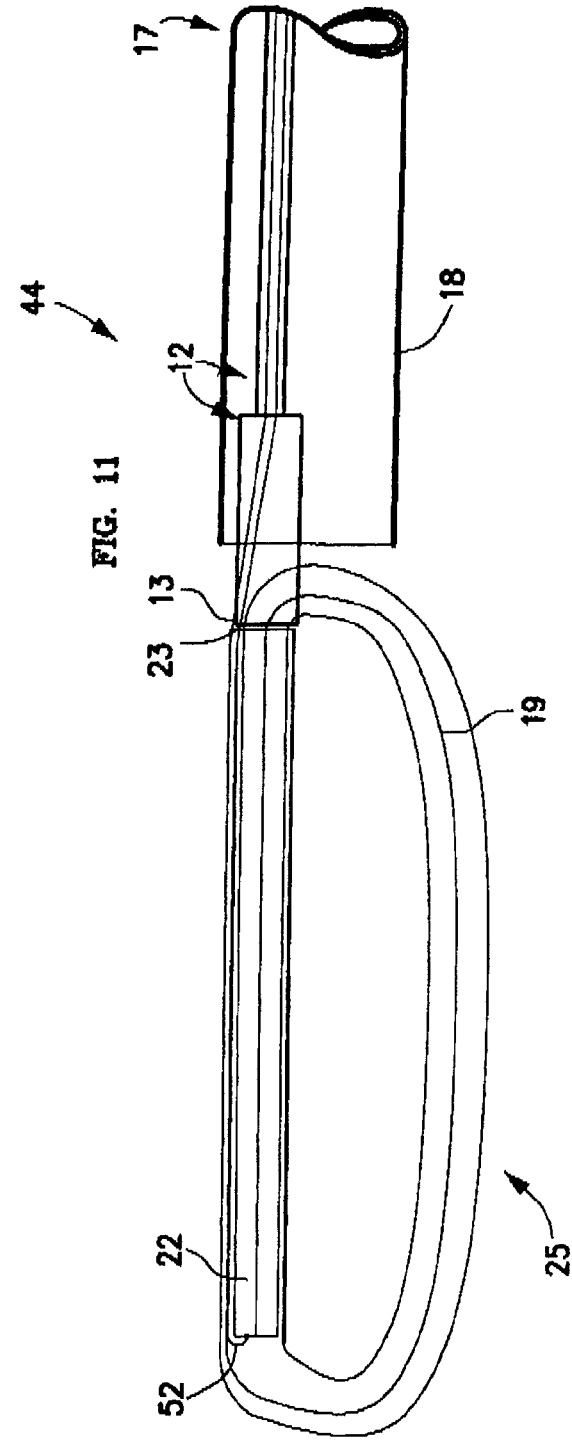

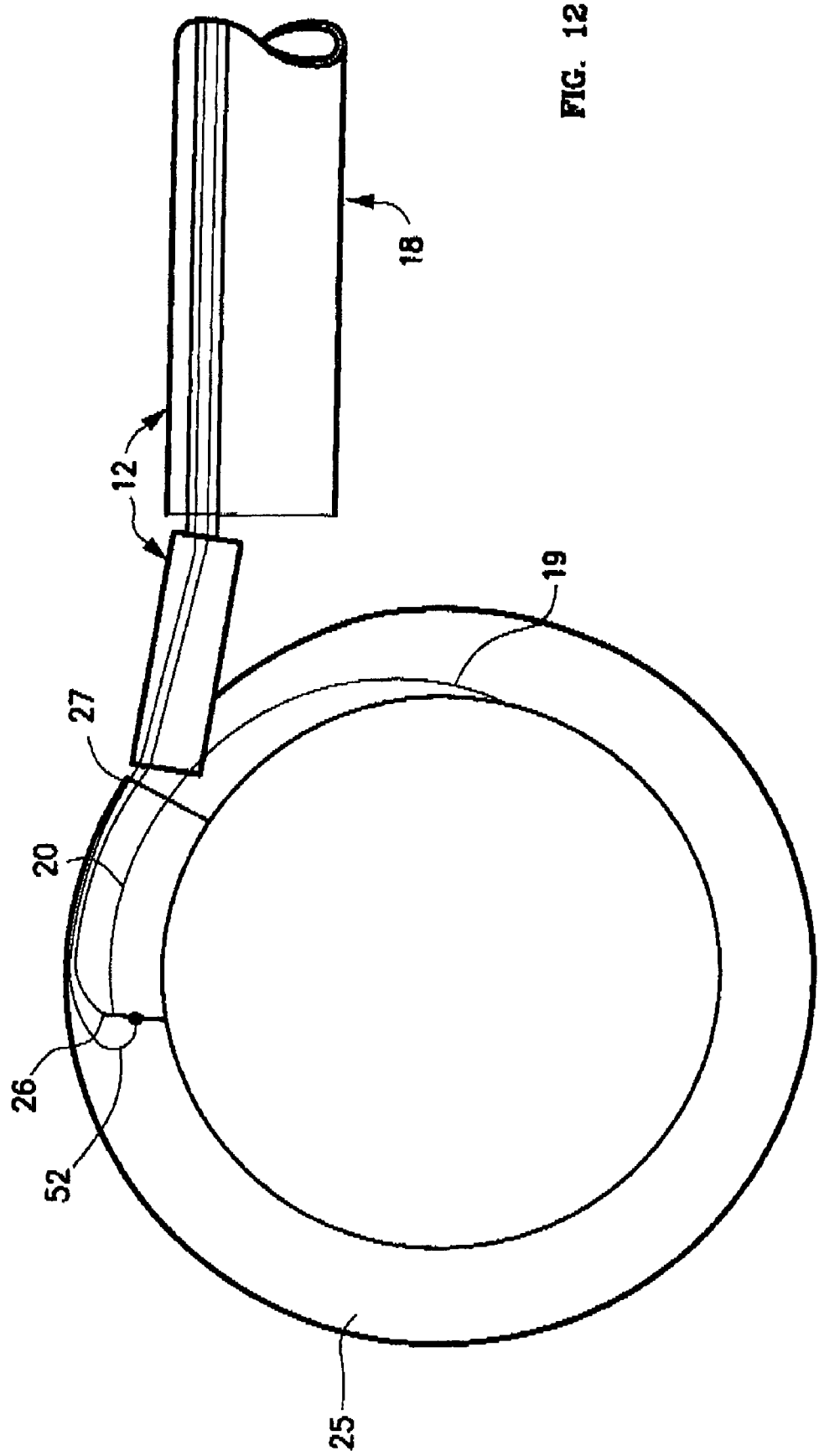

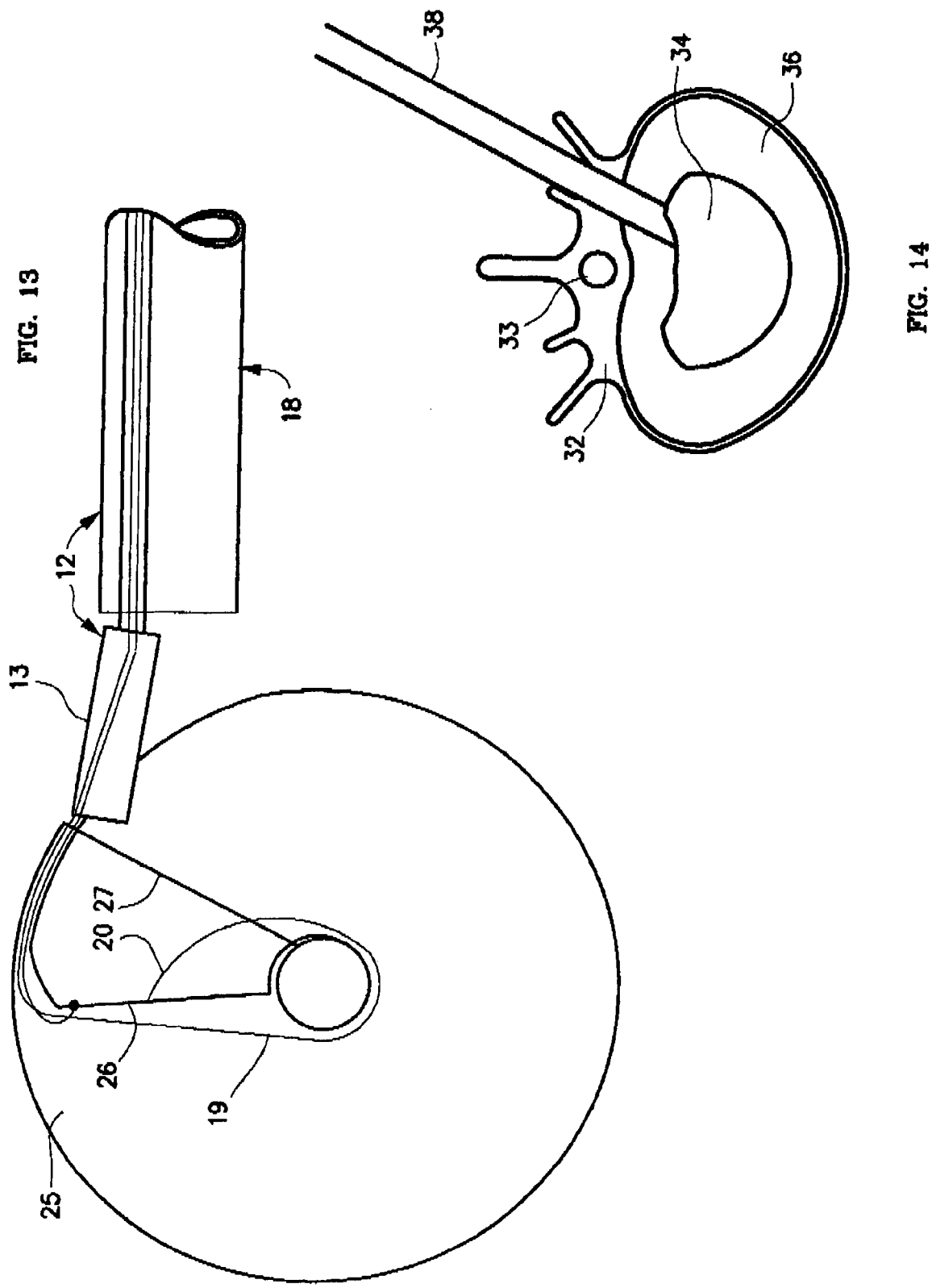

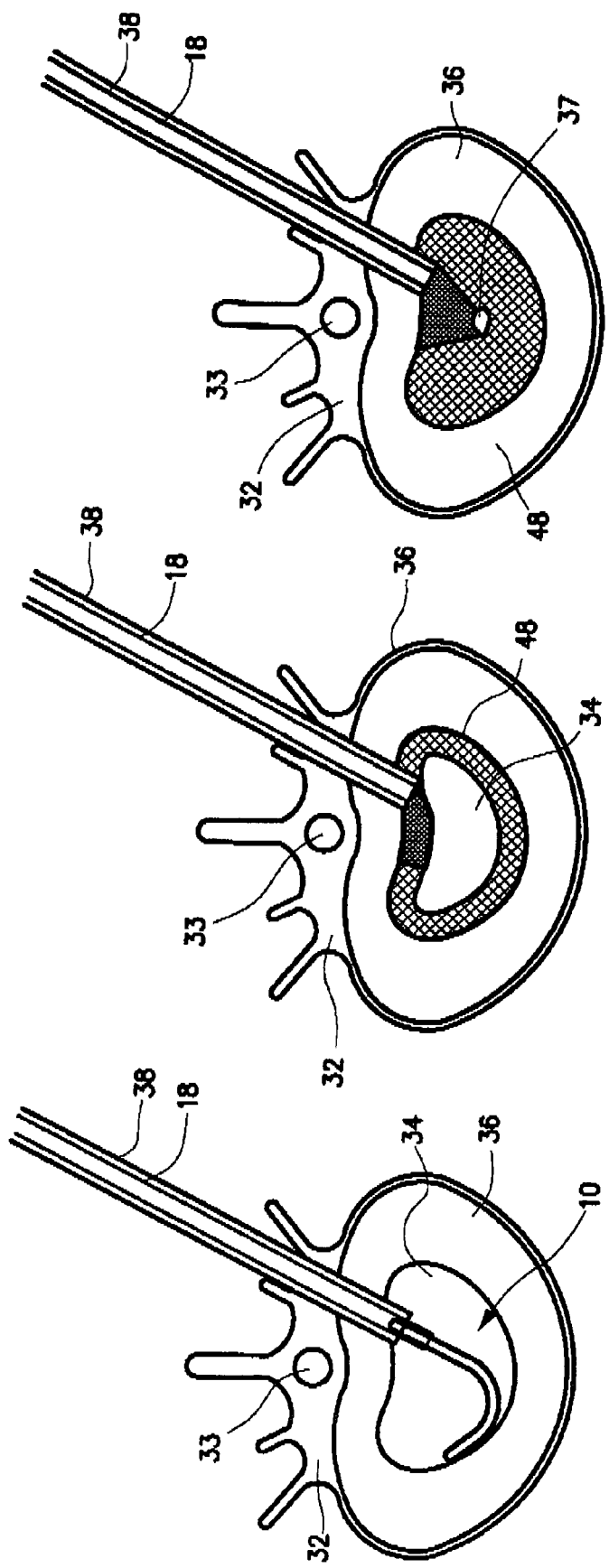

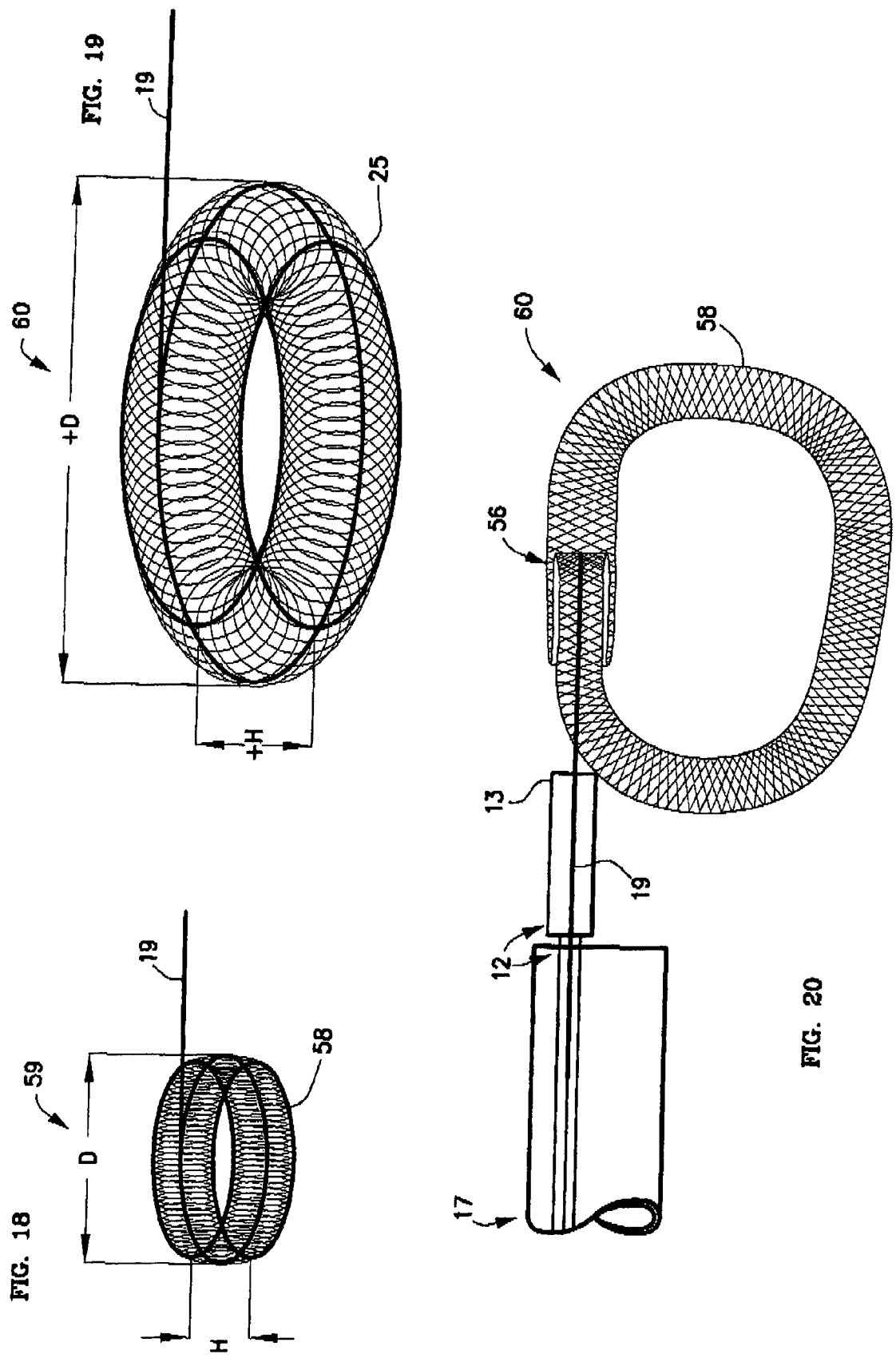

MECHANICAL APPARATUS AND METHOD FOR ARTIFICIAL DISC REPLACEMENT

CROSS-REFERENCES

The present application is a continuation-in-part of patent application Ser. No. 11/153,776 filed on Jun. 15, 2005 and Ser. No. 11/173,034 filed on Jul. 1, 2005 now U.S. Pat. No. 7,442,210. These applications are incorporated herein by this reference.

FIELD OF THE INVENTION

The present invention generally relates to devices and methods for the repair of inter-vertebral discs. More, specifically, the present invention relates to devices and methods for the treatment of spinal disorders associated with the nucleus, annulus and inter-vertebral disc.

BACKGROUND OF THE INVENTION

Inter-vertebral disc disease is a major worldwide health problem. In the United States alone almost 700,000 spine procedures are performed each year and the total cost of treatment of back pain exceeds $30 billion. Age related changes in the disc include diminished water content in the nucleus and increased collagen content by the $4^{th}$ decade of life. Loss of water binding by the nucleus results in more compressive loading of the annulus. This renders the annulus more susceptible to delamination and damage. Damage to the annulus, in turn, accelerates disc degeneration and degeneration of surrounding tissues such as the facet joints.

The two most common spinal surgical procedures performed are discectomy and spinal fusion. These procedures only address the symptom of lower back pain. Both procedures actually worsen the overall condition of the affected disc and the adjacent discs. A better solution would be implantation of an artificial disc for treatment of the lower back pain and to restore the normal anatomy and function of the diseased disc.

The concept of a disc prosthesis dates back to a French patent by van Steenbrugghe in 1956. 17 years later, Urbaniak reported the first disc prosthesis implanted in animals. Since this time, numerous prior art devises for disc replacement have been proposed and tested. These are generally divided into devices for artificial total disc replacement or artificial nucleus replacement. The devises proposed for artificial total disc replacement, such as those developed by Kostuik, that generally involve some flexible central component attached to metallic endplates which may be affixed to the adjacent vertebrae. The flexible component may be in the form of a spring or alternatively a polyethylene core (Marnay). The most widely implanted total artificial disc to date is the Link SB Charite disc which is composed of a biconvex ultra high molecular weight polyethylene spacer interfaced with two endplates made of cobalt-chromium-molybdenum alloy. Over 2000 of these have been implanted with good results. However device failure has been reported along with dislocation and migration. The Charite disc also requires an extensive surgical dissection via an anterior approach.

The approach of artificial nucleus replacement has several obvious advantages over artificial total disc replacement. By replacing only the nucleus, it preserves the remaining disc structures such as the annulus and endplates and preserves their function. Because the annulus and endplates are left intact, the surgical procedure is much simpler and operative time is less. Several nuclear prostheses can be place via a minimally invasive endoscopic approach. The nucleus implant in widest use today is the one developed by Raymedica (Bloomington, Minn.) which consists of a hydrogel core constrained in a woven polyethylene jacket. The pellet shaped hydrogel core is compressed and dehydrated to minimize size prior to placement. Upon implantation the hydrogel begins to absorb fluid and expand. The flexible but inelastic jacket permits the hydrogel to deform and reform in response to compressive forces yet constrain the horizontal and vertical expansion (see U.S. Pat. Nos. 4,904,260 and 4,772,287 to Ray). Other types of nuclear replacement have been described which include either an expansive hydrogel or polymer to provide for disc separation and relieve compressive load on the other disc components (see U.S. Pat. No. 5,192,326 to Boa). Major limitations of nuclear prostheses are that they can only be used in patients in whom disc degeneration is at an early stage because they require the presence of a competent natural annulus. In discs at later stages of degeneration the annulus is often torn, flattened and/or delaminated and may not be strong enough to provide the needed constraint. Additionally, placement of the artificial nucleus often requires access through the annulus. This leaves behind a defect in the annulus through which the artificial nucleus may eventually extrude compressing adjacent structures. What is clearly needed is a replacement or reinforcement for the natural annulus which may be used in conjunction with these various nuclear replacement devices.

Several annular repair or reinforcement devices have been previously described. These include the annulus reinforcing band described by U.S. Pat. No. 6,712,853 to Kuslich, which describes an expansile band pressurized with bone graft material or like, expanding the band. U.S. Pat. No. 6,883,520 B2 to Lambrecht et al, describes a device and method for constraining a disc herniation utilizing an anchor and membrane to close the annular defect. U.S. patent application Ser. No. 10/676,868 to Slivka et al. describes a spinal disc defect repair method. U.S. Pat. No. 6,806,595 B2 to Keith et al. describes disc reinforcement by implantation of reinforcement members around the annulus of the disc. U.S. Pat. No. 6,592,625 B2 to Cauthen describes a collapsible patch put through an aperture in the sub-annular space. U.S. patent application Ser. No. 10/873,899 to Milbocker et al. describes injection of in situ polymerizing fluid for repair of a weakened annulus fibrosis or replacement or augmentation of the disc nucleus.

Each of these prior art references describes devices or methods utilized for repair of at least a portion of the diseased annulus. What is clearly needed is an improved spinal disc device and method capable of reinforcing the entire annulus circumferentially. In addition what is clearly needed is a spinal disc device and method which may be easily placed into the inter-vertebral space and made to conform to this space. What is clearly needed is an improved spinal disc device and method capable of reinforcing the entire annulus that may be utilized either in conjunction with an artificial nucleus pulposis or may be used as a reinforcement for the annulus fibrosis and as an artificial nucleus pulposis.

SUMMARY OF THE INVENTION

The present invention addresses this need by providing improved spinal disc device and methods for the treatment of inter-vertebral disc disease. The improved device and methods of the present invention specifically address disc related pain but may have other significant applications not specifically mentioned herein. For purposes of illustration only, and without limitation, the present invention is discussed in detail with reference to the treatment of damaged discs of the adult human spinal column.

As will become apparent from the following detailed description, the improved spinal disc device and methods of the present invention may reduce if not eliminate back pain while maintaining near normal anatomical motion. The present invention relates to devices and methods which may be used to reinforce or replace the native annulus, replace the native nucleus, replace both the annulus and nucleus or facilitate fusion of adjacent vertebrae. The devices of the present invention are particularly well suited for minimally invasive methods of implantation.

The spinal disc device is a catheter based device which is placed into the inter-vertebral space following discectomy performed by either traditional surgical or endoscopic approaches. The distal end of the catheter is comprised of an expansile loop or mesh which may be increased in diameter by either advancement or retraction of a control element comprising a flexible portion of the catheter which may be manipulated by its proximal end, such proximal end remaining external to the body. The expansile loop or mesh may be formed of a woven, knitted or braided material and may be made of Nylon, Dacron, synthetic polyamide, expanded polytetrafluoroethylene (e-PTFE), polyethylene and ultra-high molecular weight fibers of polyethylene (UHMWPE) commercially available as Spectra™ or Dyneema™, as well as other high tensile strength materials such as Vectran™, Kevlar™, natural or artificially produced silk and commercially available suture materials used in a variety of surgical procedures. Alternatively the expansile loop or mesh portion of the catheter may be made of a biodegradable or bioabsorbable material such as resorbable collagen, LPLA (poly(l-lactide)), DLPLA (poly(dl-lactide)), LPLA-DLPLA, PGA (polyglycolide), PGA-LPLA or PGA-DLPLA, polylactic acid and polyglycolic acid which is broken down and bioabsorbed by the patient over a period of time. Alternatively the expansile portion of the catheter may be formed from metallic materials, for example, stainless steel, elgiloy, Nitinol, or other biocompatible metals. Further, it is anticipated that the expansile loop portion of the device could be made from a flattened tubular knit, weave, mesh or foam structure.

The expansile loop may be formed such that when the loop is diametrically contracted one end of the loop feeds into its other end, similar to a snake eating its own tail. Alternatively, the expansile loop may be formed such that when it is diametrically contracted it is in the shape of a toroid invaginating into itself. Stabilization of the outer portion of the loop and pulling out the inner portion will thereby increase the overall diameter of the loop while maintaining it as a substantially closed loop or toroid.

In one embodiment, the present invention consists of a device and method, whereby the present invention is first delivered and expanded within the vertebral space to the limits of the inner portion of the native annulus to reinforce or artificially replace the native annulus.

In another embodiment, the present invention consists of a device and method, whereby the present invention is first delivered and expanded within the vertebral space to the limits of the inner portion of the native annulus and then an injection of polymeric or hydrogel or like material is conducted to reinforce or artificially replace the native annulus.

In another embodiment, the present invention consists of a device and method, whereby the present invention is first delivered and expanded within the vertebral space to the limits of the inner portion of the native annulus and then the inner portion of the present invention is centrally expanded to the limits of an artificial nucleus concurrently or previously placed within the inter-vertebral space.

In another embodiment, the present invention consists of a device and method, whereby the present invention is first delivered within the vertebral space and into the area of the nucleus, which may have been previously removed, and expanded to the limits of the outer portion of the area of the native nucleus and then injected with a polymer or hydrogel or like material conducted to reinforce or artificially replace the native nucleus.

In another embodiment, the present invention consists of a device and method, whereby the present invention is first delivered within the vertebral space and expanded within the vertebral space to the limits of the outer portion of the native annulus and then an injection of polymeric or hydrogel material is conducted to reinforce or artificially replace the native annulus. Then the present invention is delivered into the nucleus area and expanded to the limits of the outer portion of the native nucleus or an artificial nucleus concurrently placed and then an injection of polymeric or hydrogel material is conducted to reinforce or artificially replace or reinforce the nucleus.

In another embodiment, the present invention consists of a device and method, whereby the present invention is first delivered and expanded within the vertebral space and expanded inward from the outer limits of the annulus to the point where essentially no central hole remains in the toroid and a polymeric or hydrogel or like material is injected into the expanded mesh.

In another embodiment, the present invention consists of a device and method, whereby the present invention is delivered and expanded within the vertebral space and then an injection of a bone graft material, polymeric bone graft compound, or material inducing or promoting the growth of bone such as, but not limited to growth factors, BMP or like is conducted in order to facilitate the fusion of an adjacent vertebrae.

The present invention and variations of its embodiments is summarized herein. Additional details of the present invention and embodiments of the present invention may be found in the Detailed Description of the Preferred Embodiments and Claims below. These and other features, aspects and advantages of the present invention will become better understood with reference to the following descriptions and claims.

BRIEF DESCRIPTION OF THE DRAWINGS

FIG. 1 is a cross-section view of one embodiment of the present invention with the control element attached to the interior distal end of the expansile loop and in a contracted delivery configuration.

FIG. 2 is a cross-sectional of one embodiment of the present invention with the control element attached to the interior distal end of the expansile loop and with the sheath retracted and the expansile loop exposed.

FIG. 3 is a cross-section view of one embodiment of the present invention with the control element attached to the interior distal end of the expansile loop and with the expansile in an expanded configuration.

FIG. 4 is a cross-section of the one embodiment of the present invention with the control element attached to the interior distal end of the expansile loop and with the expansile loop in an expanded and the inner circumference of the expansile loop in a contracted configuration.

FIG. 6 is a cross-section view of another embodiment of the present invention with the control element exiting the sidewall of the outer section of the expansile loop and releasably connecting to the proximal portion of the outer section of the expansile loop and with the expansile loop shown in a contracted delivery configuration.

FIG. 7 is a cross-sectional view of another embodiment of the present invention with the sheath retracted and the expansile loop exposed.

FIG. 8 is a cross-section view of the embodiment of FIG. 1 with the expansile loop in an expanded configuration.

FIG. 9 is a magnified cross-section view from FIG. 8 of the present invention showing the controlling end of the expansile loop.

FIG. 10 is a cross-section view of another embodiment of the present invention with two control elements and in a contracted delivery configuration.

FIG. 11 is a cross-sectional of another embodiment of the present invention with two control elements and with the sheath retracted and the expansile loop exposed.

FIG. 12 is a cross-section view of another embodiment of the present invention with two control elements and with the expansile loop in an expanded configuration.

FIG. 13 is a cross-section of another embodiment of the present invention with two control elements and with the expansile loop in an expanded and the inner circumference of the expansile loop in a contracted configuration.

FIG. 14 is top view cross-section view of a spinal body (vertebrae) showing the posterolateral access tube advanced into the inter-vertebral space.

FIG. 15 is a top view cross-section view of a spinal body (vertebrae) with one of the embodiments of the present invention being positioned within the inter-vertebral space of the spinal body (vertebrae).

FIG. 16 is a top view cross-section of a spinal body (vertebrae) with one of the embodiments of the present invention expanded and surrounding the nucleus section of the spinal body (vertebrae).

FIG. 17 is top view cross-section of a spinal body (vertebrae) with one of the embodiments of the present invention's outside diameter expanded and the inside diameter contracted within the inter-vertebral space of the spinal body (vertebrae).

FIG. 18 is a cross-section dimensional view of the expansile loop in a partially expanded configuration with a diameter D and a height H.

FIG. 19 is a cross-sectional dimensional view of the expansile loop in an expanded configuration with the diameter increasing +D and the height increasing +H.

FIG. 20 is a cross-section view of another embodiment of the present invention with the expansile loop in an invaginated configuration (whereby a portion of the expansile loop is bent back and entering itself) with the expansile loop in a partially expanded configuration.

DESCRIPTION OF THE PREFERRED EMBODIMENTS

Figure 5:
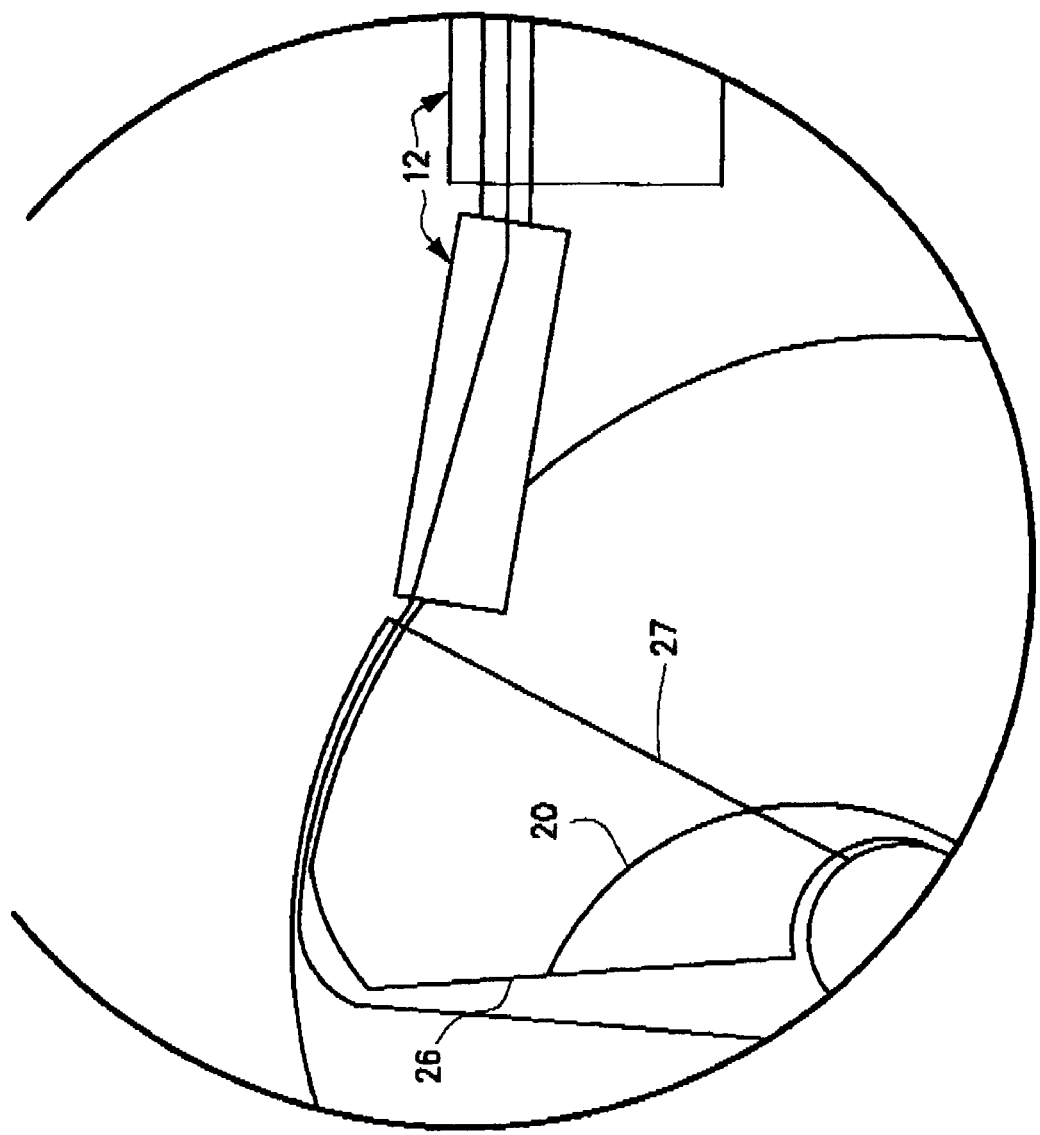
FIG. 5 is a magnified cross-section view from FIG. 4 of the present invention with the control element attached to the interior distal end of the expansile loop and showing the controlling end of the expansile loop.

One embodiment 10, 11 of the spinal disc device, as shown in FIGS. 1-5, consists of an elongated probe 15, with a proximal end 17 and a distal end 16. Referring to FIGS. 1 and 2, is can be seen that the elongated probe 15 is constructed from at least two elements, a flexible inner catheter control element 19, and a stiffer outer catheter element 12. The inner catheter control element 19 is slidably located within the outer catheter element 12. At the proximal end 17 of elongated probe 15, the inner catheter control element 19 exits from the outer catheter element 12, and can be advanced or retracted causing the distal end 20 of the inner catheter control element 19 to move in or out of the distal end 13 of the outer catheter element 12. Near the distal end 16 of the elongated probe 15, is situated an expansile, braided or woven tubular loop 24 in a contracted or delivery configuration (FIG. 1). The inner catheter control element 19 enters the expansile loop 24 near the distal end 13 of the outer catheter element 12 and slidably resides within the expansile loop 24. The distal end 22 of the expansile loop 24 is fed into the proximal end 23, of the expansile loop 24 in a manner similar to a snake eating its own tail. This results in an expansile loop 24 with an inner section and outer section as shown in FIGS. 1 and 2. A covering retractable sheath 18 is placed over the elongated probe 15 to hold it in a constrained condition for delivery into the vertebral disc. After the sheath 18 is retracted, the expansile loop 24 may be increased in circumferential diameter by withdrawing the distal end 22 of the expansile loop 24 from the proximal end 23 of the outer expansile loop 24 (FIG. 3). In this configuration, a substantially continuous interior chamber 28 is now defined within the expanded expansile loop 25. The outer catheter element 12 terminates at its distal end 13 and is removably attached to the proximal end 23 of the outer section of the expanded expansile loop 25. The inner catheter control element 19, in the form of a filament, guidewire or flexible tube, slidably extends from the proximal end 17 of the catheter or probe 15, through the outer catheter element 12, and exiting the outer catheter element at its distal end 13. The inner catheter element then enters the inside of the outer section of the expansile loop at its proximal end 23. The inner catheter control element 19 may be looped one, less than one, or more than one time within the expansile loop 24, 25 between the inner and outer portions of the loop prior to the inner catheter element 19 or control element terminating within the expansile loop 24, 25 at its distal end 22, 26. The inner catheter control element 19 is then attached to the expansile loop 24, 25 at the distal end 22, 26 of the inner section of the expansile loop 24, 25.

The inner catheter control element can be made of a flexible yet longitudinally incompressible material such as, but not limited to, a stainless steel or Nitinol wire of 0.010"-0.040" diameter. Slidably advancing the inner catheter element 19 through the outer catheter element 12 while holding the proximal portion of the outer section of the expansile loop 23, 27 in place will result in the inner section of the expansile loop 24, 25 pulling out of the outer section of the expansile loop 24, 25. This will result in the overall diametric expansion of the expansile loop 24, 25. As shown in FIG. 4, once expansion of the outer circumference of the expansile loop 25 is achieved and fixed, pulling out the inner catheter control element 19 while holding the outer section 27 of the expansile loop 25 fixed, contracts the inner circumference of the expansile loop 25 while expanding its height. Expansion of the expansile loop 25 into the vertebral space is achieved by the spring nature of the expansile loop's 24, 25 material construction or by advancing the inner catheter control element 19 while holding the proximal outer section of the expansile loop 23 fixed. Next, pulling on the inner catheter control element 19 while holding the proximal outer section 27 of the expansile loop 25 fixed, the interior circumference of the expansile loop 25 contracts toward the center of the expansile loop 25 while the height of the expansile loop 25 increases.

FIG. 5 is a magnified cross-section view from FIG. 4 of this present invention embodiment with the control element attached to the interior distal end 26 of the expansile loop 25. This Figure shows the controlling end of the expansile loop 25 and the physical relationship between the distal end 20 of the inner catheter 19, distal 26 and proximal end 27 of the expansile loop 25, and outer catheter element 12.

The outer catheter element 12 used for delivery of the expansile loop 24 should be sufficiently stiff to allow retraction of the inner catheter control element 19 without collapse or kinking. The inner catheter control element 19 must be sufficiently flexible to circle around the expansile loop 24 and attains a relatively small radius without kinking yet have sufficient tensile strength to resist breakage when pulled from its proximal sections. The outer catheter element 12 can be fabricated from polymeric materials including, but not limited to, Nylon, Dacron, synthetic polyamide, expanded polytetrafluoroethylene (e-PTFE), polyethylene and ultra-high molecular weight fibers of polyethylene (UHMWPE), or metallic materials, including but not limited to, stainless steel, cobalt-chrome alloy, titanium, titanium alloy, or nickel-titanium shape memory alloys, among others that have sufficient kink resistance and tensile strength. The inner catheter control element 19 can be manufactured from Nylon, Dacron, synthetic polyamide, expanded polytetrafluoroethylene (e-PTFE), polyethylene and ultra-high molecular weight fibers of polyethylene (UHMWPE) or from metallic materials including, but not limited to, stainless steel, cobalt-chrome alloy, titanium, titanium alloy, or nickel-titanium shape memory alloys, among others. The elements manufactured from metallic materials have a diameter from 0.001" to 0.020" and preferably from 0.004" to 0.010". The elements manufactured from polymeric materials have a diameter from 0.005" to 0.040" and a preferred diameter from 0.010" to 0.020".

The expansile loop 24, 25 is fabricated as a knit, weave or braid and can be constructed from non-degradable materials. Suitable non-degradable materials for the expansile loop 24, 25, include, but are not limited to, Nylon, Dacron, synthetic polyamide, expanded polytetrafluoroethylene (e-PTFE), polyethylene and ultra-high molecular weight fibers of polyethylene (UHMWPE) commercially available as Spectra™ or Dyneema™, as well as other high tensile strength materials such as Vectran™, Kevlar™, natural or artificially produced silk and commercially available suture materials used in a variety of surgical procedures. The expansile loop 24, 25 fabricated as a weave or braid and can be constructed from biodegradable or bioabsorbable materials. Suitable biodegradable and bioabsorbable materials for the expansile loop 24, 25 include, but are not limited to, resorbable collagen, LPLA (poly(l-lactide)), DLPLA (poly(dl-lactide)), LPLA-DLPLA, PGA (polyglycolide), PGA-LPLA or PGA-DL-PLA, and biodegradable sutures made from polylactic acid and polyglycolic acid.

In addition, for some embodiments, suitable metallic materials for the expansile loop 24, 25 may be used that include, but are not limited to, stainless steel, cobalt-chrome alloy, titanium, titanium alloy, or nickel-titanium shape memory alloys, among others. It is further contemplated that the metallic mesh can be interwoven with non-resorbable polymers such as nylon fibers, carbon fibers and polyethylene fibers, among others, to form a metal-polymer composite weave. Further examples of suitable non-resorbable materials include DACRON and GORE-TEX. One feature of the expansile loop 24, 25 is that it needs to have pore sizes or openings that are small enough to hold the filling material or nucleus from extruding out and large enough to maintain flexibility and expansion characteristics.

In another embodiment the distal end 13 of the outer catheter element 12 resides around the inner catheter control element 19. The outer catheter element 12 is held in a constant relationship or releasably affixed to the proximal end 23 of the outer section of the expansile loop 24. In this embodiment the inner catheter control element 19 is in the form of a very flexible element which enters the proximal opening in the outside section of the expansile loop 23, loops one, less than one or more than one time around the inside of the outside section of the expansile loop 24 and terminates attaching at the distal end 22 of the inside section of the expansile loop 24. The direction of rotation of the flexible control element 19 (measured from distal end of the control element 20 to the proximal end 21 is in the opposite rotational direction as the direction of rotation of the inside section of the expansile loop 24, as it enters and loops around the outside section of the expansile loop 24. Upon retraction of the proximal end 21 of the inner catheter control element 19, back out of the outer catheter element 12, the distal end 13 of the outer catheter element 12 stabilizes and holds the outer section 23 of the expansile loop 24 in place while the inner section 22 of the expansile loop 24 is pulled out of the outer section, resulting in an increase in the diameter of the expansile loop 24. Once the expanded expansile loop 25 has reached its maximum diameter, determined either by the confines of the space into which it is expanding or by the exit point of the control filament through the proximal end 27 of the expanded expansile loop 25, continued retraction of the inner catheter control element 19 will result in the inner catheter control element 19 producing tension on the inner circumference of the expanded expansile loop 25. The inner circumference of the expanded expansile loop 25 will contract towards the middle of the expanded expansile loop 25 and the expanded expansile loop's 25 height will increase. Due to the woven or braided nature of the tubular expansile loop 24, 25, the expanded expansile loop 25, will remain generally in the shape of a toroid both upon its circumferential expansion and its central contraction.

An additional embodiment 39, 40 of the expansile loop device used for repair or replacement of the annulus fibrosis of the spine can be understood by referring to FIGS. 6-9. As shown in FIGS. 6-8, the inner catheter control element 19 is looped around and exits through the wall of the outer section of the expansile braided loop 24 near the attachment of the outer catheter element 12 to the proximal end 23 of the outer section of the expansile loop 24. The inner catheter control element 19 is then affixed to the outer catheter element 12, at this point using either a knot or a releasable or removable junction or passes proximally through the outer catheter element 12. A covering retractable sheath 18 is placed over the elongated probe 15 to hold it in a constrained condition for delivery into the vertebral disc. After the sheath 18 is retracted, a "snare" or loop is formed by the proximal portion of the inner catheter control element 19 being slidably located within the outer catheter element 12 and the expansile loop 24. If the inner catheter control element 19 is of sufficient stiffness, for example but not limited to, a metallic guidewire of 0.010"-0.040" diameter, the snare and the expansile loop 24 may be opened by advancing the proximal portion 21 of the inner catheter control element 19 while holding the outer catheter element 12 and the proximal end of the expansile loop 23 in place. This opening of the circumference of the snare formed by the inner catheter control element 19 will result in an expansion of the circumference of the expansile loop 24 as the inner portion of the expansile loop 24 pulls out of its outer portion. Once the limits of expansion of the expanded expansile loop 25 have been reached, the inner catheter control element 19 may be detached at the junction or connection of the outer catheter 12 and the proximal end of the expanded expansile loop 27 and slidably retracted out of the expanded expansile loop 25 leaving behind a circumferentially expanded expansile loop 25.

In an alternative embodiment of the present invention for annular repair or replacement, the inner catheter control element 19 is run inside of the expansile loop 24, 25 which is looped and exits first the distal end of the inner section of the braided loop 22, 26 and then exits through the wall of the outer portion of the braided loop 23, 27 prior to its attachment to outer catheter element 12. The inner catheter control element or filament 19 may make one, less than one or more than one loop inside of the expansile loop 24, 25 prior to exiting and attaching to catheter element 12. In this manner the inner catheter control element 19 forms a "snare" or loop of one or multiple turns. If the inner catheter control element 19 is of sufficient stiffness, for example but not limited to, a metallic guidewire of 0.010"-0.040" diameter, the snare may be opened by advancing the proximal portion of the inner catheter control element 21 while holding the outer catheter element 12 and proximal end of the expansile loop 23, 27 in place. This opening of the circumference of one or more loops of the snare formed by the inner catheter control element 19 will result in an expansion of the circumference of the expansile loop 24, 25 as the inner portion of the expansile loop 24, 25 pulls out of its outer portion. Once the limits of expansion of the expansile loop 24, 25 have been reached, the inner catheter control element 19 may be pulled back into the catheter element 12 by pulling on its proximal portion 21. This causes one or more loops of the snare becoming smaller pulling on the inner circumference of the expanded expansile loop 25 resulting in a contraction of the central space in the middle of the expanded expansile loop 25. Due to the woven or braided nature of the expansile loop 24, 25, the expansile loop 24, 25, will remain generally in the shape of a toroid both upon its circumferential expansion and its central contraction.

As shown in FIGS. 10-13, another embodiment 43, 44 of the present invention comprises an elongated probe 15, with a proximal end 17 and a distal end 16. Referring to FIGS. 10 and 11, a first inner catheter control element 19 is slidably located within the outer catheter element 12. At the proximal end 17 of elongated probe 15, the inner catheter control element 19 exits from the outer catheter element 12, and can be advanced or retracted causing the distal end 20 of the inner catheter control element 19 to move in or out of the distal end 13 of the outer catheter element 12. The first inner catheter control element 19, in the form of a filament, guidewire or flexible tube, slidably extends from the proximal end 17 of the probe 15, through the lumen of the outer catheter element 12, and exiting the outer catheter element 12 at its distal end 13. The inner catheter control element 19 then enters the inside of the outer section of the expansile loop 24 at its proximal end 23. The inner catheter control element 19 may be looped one, less than one, or more than one time within the expansile loop 24 between the inner and outer portions of the expansile loop 24 prior to the inner catheter element or control element 19 terminating within the expansile loop 24. The inner catheter control element 19 is then attached to the expansile loop 24 at its distal end 22. This embodiment also includes a second inner catheter control element 52 which extends from the proximal end 17 of the catheter or probe 15, through the outer catheter element 12, and exiting the outer catheter element 12 at its distal end 13. The second inner catheter control element 52 then enters the outside of the outer section of the expansile loop 24 and is attached to the distal end 22 of the expansile loop 24. A covering retractable sheath 18 is placed over the elongated probe 15 to hold it in a constrained condition for delivery into the vertebral disc. After the sheath 18 is retracted, the second interior catheter control element 52 is pulled back into the outer catheter control element 12 by pulling on its proximal end. This causes the distal end of the expansile loop 22 to be pulled from inside the outer portion of the expansile loop 24 expanding the outer circumference of the expansile loop 24 (See FIG. 12). Now referring to FIG. 13, the first inner catheter control element 19 may be pulled back into the outer catheter element 12 by pulling on its proximal end. This will result in a pulling in of the center of the expansile loop 25 towards the middle of the loop and contraction of central space in the middle of the expansile loop 25. Due to the woven or braided nature of the tubular expansile loop 24, 25, the expansile loop 24, 25, will remain generally in the shape of a toroid both upon its circumferential expansion and its central contraction.

In another embodiment 59, 60 as represented in FIGS. 18-20, the contracted configuration of the expansile loop 58 comprises an expansile loop 58 which has a portion folding back into itself or invaginated 56 (see FIG. 20). This forms a complete toroid with a portion invaginated to form a diametrically contracted toroid with an inner section and an outer section that are continuous with each other. Pulling on the inner catheter control element 19 in the manner previously described will function to increase the diameter (+D) and increase the height (+H) of the expanded expansile loop 25 as the central portion of the toroid is pulled towards the center.

The entire expansile loop assembly 10 including the circumferentially contracted braided expansile loop 24, and inner catheter control element 19, may now be compressed into the distal outer catheter element, a sheath 18 or alternatively into an access tube 38 of approximately 3-20 mm diameter for ease of placement. The access tube 38 may be formed from any suitable material, as the present invention is not limited in this respect. Thus, the access tube 38 may be formed from a plastic material, such as a polycarbonate, or a metal material, such as stainless steel, or any suitable combination of materials. In addition, the posterolateral access tube 38 may be formed of a material that can be readily sterilized. Further, the elongated probe 15 may be formed as a single use device such that resterilization is not required after use. The posterolateral access tube 38 gains access to the vertebrae generally using a posterior approach (FIG. 14).

As shown in FIG. 15, the posterolateral access tube 38 has gained access to the vertebrae 32, having a spinal cord 33, an annulus 36 and a nucleus area 34. Once in proper position in the vertebrae 32 of a patient, the expansile loop 24 may be ejected into the nucleus area 33 or the annulus area (not shown in this Figure) from the distal end of the outer catheter element 13, sheath 18 or access tube 38 by retracting the outer catheter element 12 or sheath 18 and simultaneously holding the inner catheter 19 and expansile loop 24 in a fixed position. Alternatively, an additional "pusher" element (not shown) can be advanced distally into the outer catheter element 12 or sheath 18 or access tube and eject the expansile loop 24, catheter element 12 and the distal inner catheter control element 20 from the end of the sheath 18. As previously described in the embodiments above, the expansile loop 24 may now be circumferentially expanded by either pulling on or pushing the inner catheter control element 19 in the manner described above. Furthermore, if it is desired that the central portion of the braided expansile loop 24 become circumferentially contracted, pulling on the inner catheter control element 19 as described above will accomplish this feature.

Now referring the FIG. 16, the expanded expansile loop 25 achieves the desired outer circumferentially expanded and inner circumferentially contracted size 48, when the inner catheter control element 19 is locked or tied in place with a knot. This can also be accomplished by a locking junction located at the outer catheter element 12. The distal portions 20 of the external inner catheter control element 19 can now be disconnected or cut from a connector or proximal to the knot. The connector or knot is also separated from the distal outer catheter element 12. This then leaves an outer circumferentially expanded and inner circumferentially contracted expansile loop 25 in place as a closed loop in the desired location (shown in FIG. 16 expanded with the nucleus area 34) within the inter-vertebral space.

Figure 21:
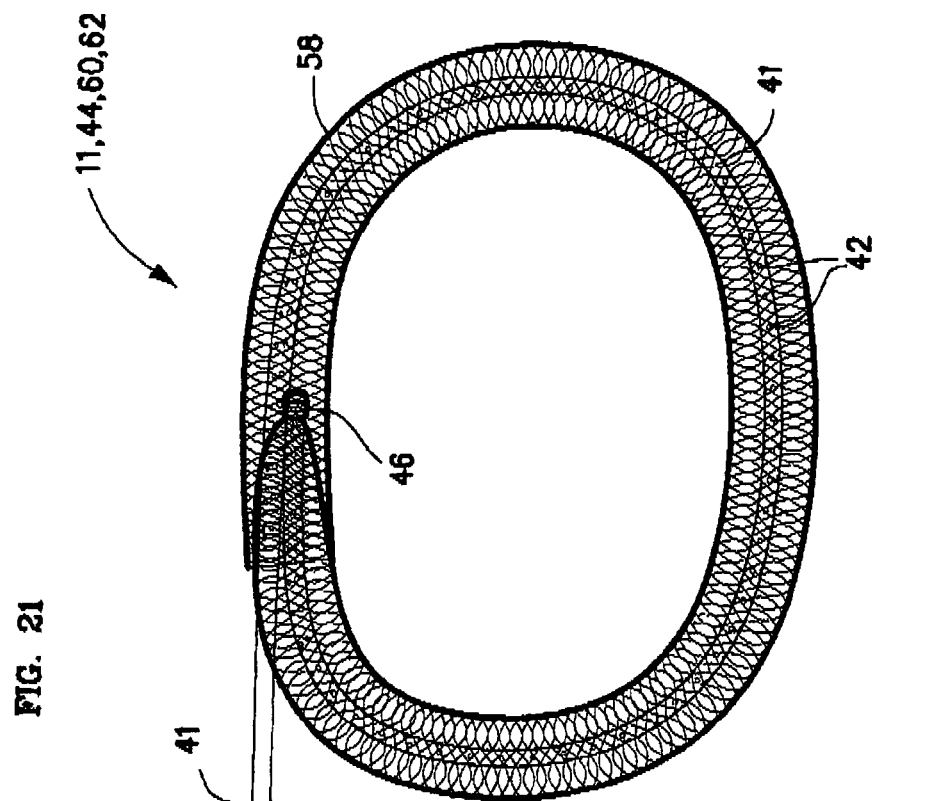
FIG. 21 is a cross-sectional view of additional feature of the present invention with an inner catheter or control element having a plurality of holes for delivery and injection of biomaterials.

As represented in FIG. 21 an additional feature of the present invention with an inner catheter control element 41 having a plurality of distal holes 42 for delivery and injection of biomaterials which can be utilized with the embodiments of the present invention. The inner catheter control element 41 with holes 42 comprises a tubular structure with a central lumen from the proximal end 17 of the outer catheter element 12 communicating with side holes in the distal end 13. The proximal end of the inner catheter or control element may be fitted with an injection device (e.g. syringe). The inner catheter control element 41 is contained within the continuous interior chamber of the expanded expansile loop 58. The holes 42 in the inner catheter control element 41 are designed to be only within the continuous inner chamber. Furthermore, it is anticipated that the holes can be of different size along the length of the inner catheter control element to equalize biocompatible material delivery (e.g. larger holes at the distal end, smaller holes at the proximal end). In addition, it is anticipated that the holes can be in various configurations, e.g. oval, or can be a plurality of slots or other similar opening.

Figure 22:
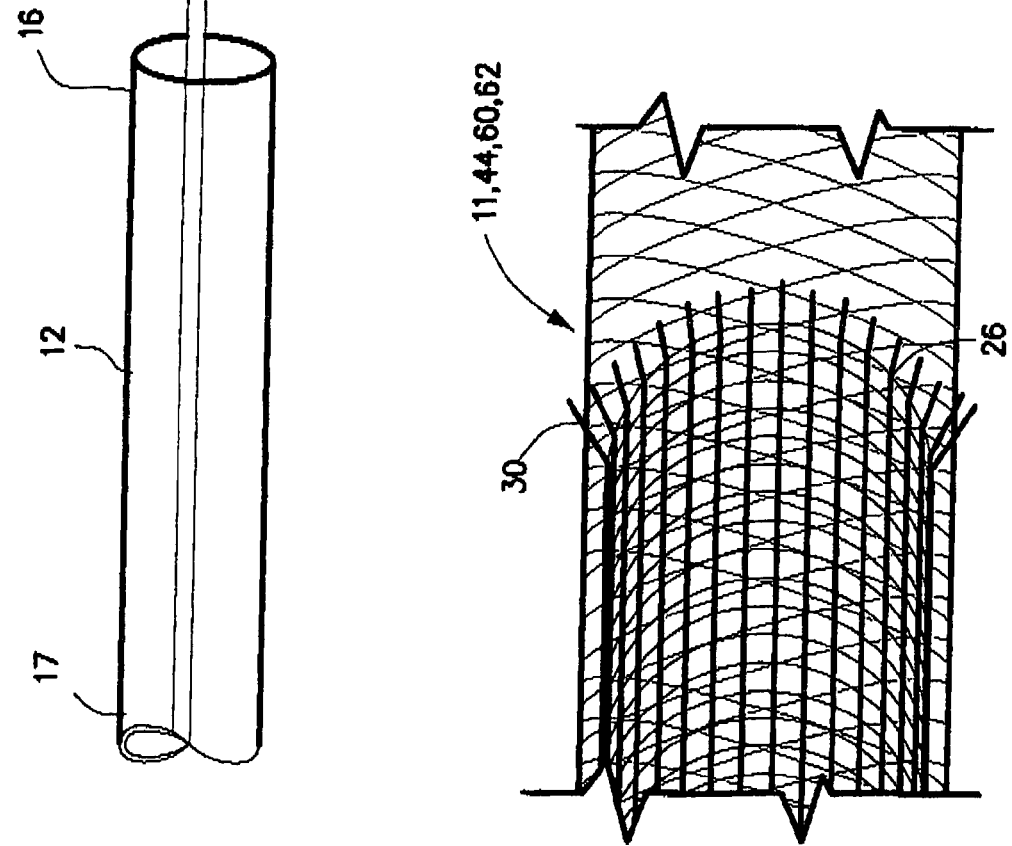
FIG. 22 is a perspective view of an element of the present invention whereby locking elements on the distal end of the expansile interior loop are engaged to the expansile outer loop.

FIG. 22 is another feature of the present invention that can be used with several of the embodiments 11,44,60,62 whereby non-permanent locking elements 30 on the distal end of the expansile interior loop are engaged to the distal end 26 of the expansile outer loop. The locking elements are extended portions of one end of the braid or loop which interlock with the braid or loop pattern. The locking elements function to maintain a desired diameter of the expansile loop after expansion.

In one method of clinical use, the nucleus of the damaged disc has been previously removed by discectomy techniques either through an anterior, posterior or posterolateral surgical approach. The expansile loop annular repair or replacement device 10 in its compressed configuration within the outer catheter element 12 or sheath 18 is advanced through an access tube or cannula previously placed into the inter-vertebral space. This cannula may access the inter-vertebral space from a posterior, posterolateral or anterior approach that is well known to physicians skilled in the art. The present invention 10 is then advanced into the inter-vertebral space through the access tube 38. Once the distal expansile loop 24 is advanced through the access tube 38 into the vertebral space it is diametrically expanded by either retraction or advancement of the inner catheter control element 19 in the manner previously described. The distal expansile loop 25 expands to the limits of the inner portion of the remains of the native annulus and remains diametrically expanded and transversely contracted as illustrated in FIG. 6. Any of a number of previously described artificial nuclei puposi may then be placed in the center of the diametrically expanded expansile loop 48 either via direct visualization from the traditional surgical approach or via endoscope from a posterolateral approach through the foramina or form a posterior approach. These artificial nuclei may then be allowed to expand either through the absorption of liquids, as is the case for hydrogel based devices, or through the injection of material into the nuclear prosthesis.

Once the nuclear replacement is in place, any remaining space between the nuclear replacement and the expansile loop annular replacement device may be reduced or eliminated by centrally contracting the inner circumference of the toroid formed by the expansile loop device. This is accomplished in the manner previously described by pulling back the inner catheter control element resulting in contraction of the inner circumference of the device until it abuts the nuclear replacement. The braided design of the expansile braided loop 48 will also allow it to flex and bend to conform to the inter-vertebral space. By properly selecting the material from which the expansile braided loop is constructed and by properly selecting the design of braid for its manufacture as previously described, the expansile braided loop will now function as a complete circumferential support for the artificial nucleus. The expansile braided loop will prevent extrusion of the artificial nucleus through any defects in the remaining native annulus and act to stabilize the artificial nucleus during both bending and motion of the spine and throughout the healing process. The braided design of the expansile loop will also permit it to flexibly bend as the central nucleus replacement expands and swells to its final size. The braided design of the expansile loop will also permit tissue in growth to occur as healing occurs. This will result in stabilization of the artificial nucleus.

In an alternative method, once the expansile braided loop 48 has been expanded to fill the inter-vertebral space between the artificial nucleus and the native vertebrae and remaining native annulus fibrosis, the expansile loop 48 may be filled with a suitable biologically compatible material. Such suitable materials that can be directly injected through the inner catheter control element 19 if it includes a central lumen and openings connecting with the interior chamber of the expansile braided loop as illustrated in FIG. 11. Alternatively, the biocompatible materials can be injected using a separate catheter element which can be advanced along the inner catheter control element into the interior chamber of the expansile braided loop. Alternatively, the biocompatible materials could be injected into the interior chamber of the expansile braided loop using a separate catheter or injection needle which pierces the side of the braided loop once it is expanded and in place in the inter-vertebral space. Biocompatible materials which may be injected include biocompatible viscoelastic materials such as hydrophilic polymers, hydrogels, homopolymer hydrogels, copolymer hydrogels, multi-polymer hydrogels, or interpenetrating hydrogels, acrylonitrile, acrylic acid, acrylamide, acrylimidine, including but not limited to PVA, PVP, PHEMA, PNVP, polyacrylamides, poly (ethylene oxide), polyvinyl alcohol, polyacrylonitrile, and polyvinyl pyrrolidone, silicone, polyurethanes, polycarbonate-polyurethane (e.g., Corethane) other biocompatible polymers, or combinations thereof. The viscosity of the injected fluids must allow them to be injected either via catheter or needle into the braided expansile loop. The injected biocompatible material must cure or polymerize in situ within the expansile braided loop and within the disc space. Such in situ curing of the biocompatible material may be the result of mixing of multiple components and polymerization, temperature change in going from room to body temperature or elevated to body temperature, or other forms of energy such as light or electricity applied to the injected material.

In addition, suitable materials that can be placed directed into the expansile loop 48 and allowed to expand through the absorption of liquids such as water include, but are not limited to, swelling hydrogel materials (e.g. polyacrliamide, polyacrylonitrile, polyvinyl alcohol or other biocompatible hydrogels). Examples of suitable materials for solid or semisolid members include solid fibrous collagen or other suitable hard hydrophilic biocompatible material. The swelling of these materials may result in further expansion of the expansile braided loop and an increase in the inter-vertebral disc height.

In some cases, a multiphase system may be employed, for example, a combination of solids, fluids or gels may be used. Such materials may create primary and secondary levels of flexibility within the braided expansile loop and within the vertebral disc space.

For example, the hydrogel materials (e.g. polyacrylamide, polyacrylonitrile, polyvinyl alcohol or other biocompatible hydrogels or combinations can be dissolved in a solvent, such as dimethylsulfoxide, analogues/homologous of dimethylsulfoxide, ethanol, ethyl lactate, acetone, glycerin or combinations thereof. Small amounts of water could also be added to the solvent/hydrogel combination to adjust the solutions viscosity. This solvent/hydrogel combination can be injected into the inter-vertebral space to replace the nucleus, the annulus, or both the nucleus and annulus. The expansile loop 48 will assist in containing and supporting the solvent/hydrogel combination. After delivery, the solvent is replaced by bodily fluids and the hydrogel precipitates out of solution into a hydrated solid. The solvent is adsorbed into the body tissues. Introducing an aqueous solvent, such as water or saline, into the inter-vertebral space containing the solvent/hydrogel combination can be performed to increase the precipitation speed of the hydrogel. This second step facilitates the precipitation or solidification of the hydrogel material which swells and fills the desired inter-vertebral space.

Once the expansile loop 48 is filled with a suitable material and the material has cured or partially polymerized, the inner catheter control element or filament 19 can be withdrawn by removing its distal connection to the junction point with the outer catheter element 12 or at its termination within the braided expansile loop and pulling the inner catheter control element out of the expansile loop. Alternatively, the inner catheter control element 19 may be cut off or disconnected at its entry point into the expansile loop. This leaves a complete toroid without defect, formed of the expansile loop in place to act as an annular reinforcement or replacement which may or may not surround an artificial nucleus device.

In another method of clinical use, after the braided expansile loop 48 has been expanded to its maximum diametric dimension, acting as a reinforcement or replacement for the damaged native annulus, the device may be centrally circumferentially contracted, as previously described, to fill any remaining space previously occupied by the native nucleus prior to nuclectomy. The braided expansile loop 48 expands to the limits of the remains of disc space and the remains of the native nucleus and annulus and remains diametrically expanded and centrally circumferentially contracted. Now the braided expansile loop area may be filled with a biomaterial or any suitable material (as described above), as the present invention is not limited in this respect. In addition to the materials disclosed for annulus replacement, additional suitable fluid materials for nucleus and annular replacement include, but are not limited to, various pharmaceuticals (steroids, antibiotics, tissue necrosis factor alpha or its antagonists, analgesics); growth factors, genes or gene vectors in solution; biologic materials (hyaluronic acid, non-crosslinked collagen, fibrin, liquid fat or oils); synthetic polymers (polyethylene glycol, liquid silicones, synthetic oils); and saline.

Once the expansile loop is filled with a suitable material in the central and circumferentially contracted nuclear area and the annular area, the inner catheter control element 19 can be withdrawn by removing its distal connection to the junction point with the outer catheter element 12 and pulling the inner catheter control element out of the expansile loop. Alternatively the inner catheter control element or filament 19 may be disconnected from its attachment to the distal inner braided expansile loop prior to its removal. Alternatively, the inner catheter control element or filament 19 may be cut off at its entry point into the outer section of expansile loop using a surgical tool. This leaves a complete toroid, without defect, formed of the expansile loop in place to act as an annular and nucleus reinforcement or replacement.

In another method of clinical use, the present invention can be advanced into the vertebral space once a nuclectomy has been performed. Once the braided expansile loop 24 is advanced into the vertebral space, it is diametrically expanded in the manner previously described. The braided expansile loop 25 expands to the limits of the out portion of the remains of the native nucleus and remains diametrically expanded and transversely contracted. Now the braided expansile loop 48 may be filled with a biomaterial of any suitable material, such as those previously noted, as the present invention is not limited in this respect. This injected material is allowed to cure or polymerize to some extent, and then the central portion of the expansile loop is circumferentially contracted in the manner previously described. At this point the central nuclear area of the vertebral space is filled with the expanded mesh. This central portion can then be filled with biomaterial or any suitable material, such as those previously noted, as the present invention is not limited in this respect. In addition to the materials disclosed for annulus repair or replacement, additional suitable fluid materials for nucleus replacement include, but are not limited to, various pharmaceuticals (steroids, antibiotics, tissue necrosis factor alpha or its antagonists, analgesics); growth factors, genes or gene vectors in solution; biologic materials (hyaluronic acid, non-crosslinked collagen, fibrin, liquid fat or oils); synthetic polymers (polyethylene glycol, liquid silicones, synthetic oils); and saline.

Once the braided expansile loop is filled with a suitable material in the nucleus area, the inner catheter control element 19 can be withdrawn by removing its distal connection to the junction point with the outer catheter element 12 or its distal connection with the distal inner expansile loop, and pulling the inner catheter control element 19 out of the expansile loop. Alternatively, the inner catheter control element or filament 19 may be cut off at its entry point into the expansile loop using a surgical tool. This leaves a complete toroid, without defect, formed of the expansile loop in place to act as an annular reinforcement or replacement and/or nucleus reinforcement or replacement. It also allows the annular area of the device on the periphery and the nucleus portion of the device in the central region to have different physical properties dependent on the differential biocompatible materials injected into each region.

In an additional method of clinical use, once the nucleus of the disc has been removed, the present invention 10 is advanced into the inter-vertebral space. The braided expansile loop 24 is diametrically expanded in the manner previously described. The distal interior braided expansile loop 25 is pulled out of the outer expansile loop and the overall expansile loop diametrically expands to the limits of the inner portion of the native annulus. Next the inner catheter control element 19 is pulled back out of the expanded expansile loop and the inner potion of the inner catheter or filament loop 19 pulls in the inner circumference of the expansile loop, making the central hole smaller and the braided expansile loop 48 transversely wider to better fill the central defect in the vertebral space. This expanded braided expansile loop 48 may be used to contact a central prosthetic nucleus previously placed in the middle of the braided expansile loop. In the case where no additional nucleus prosthesis is desired, the central portion of the braided expansile loop can be been expanded to the point where essentially no central hole 37 remains in the toroid. The fully expanded braided expansile loop can now be injected with a suitable biocompatible material (as described above) which will expand or cure in situ as previously described. In this case the present invention will function as both a prosthetic annulus and a prosthetic nucleus and its load bearing properties will be dependent on the properties of the polymer chosen to fill the expansile loop.

Additionally, a hydrogel, polymer or biocompatible material may be injected into the interior chamber of the expansile loop such that the biocompatible material has the capacity to swell or increase in size as the result of absorbing water or liquid. This would result in further expansion of the expansile braided loop and an increase in the inter-vertebral disc height.

In another method of clinical use, the intended treatment is to fuse two adjacent vertebrae using the present invention 10. Again using the illustration in FIG. 10, the end of the inner catheter control element 19 is attached to the interior and distal end 22 of the braided expansile loop 24. To expand the diameter of the expansile loop one merely needs to stabilize the proximal portion or outer end 23 of the braided expansile loop and pull back the inner catheter control element or filament 19 or wire. This will result in the inner section of the braided expansile loop pulling out of the outer section of the braided expansile spiral as the wire is retracted. Once the desired outer diameter of the braided expansile loop 48 is achieved, the central portion of the braided expansile loop 48 may be contacted by pulling the same inner catheter control element 19 further back out of the proximal portion of the braided expansile loop. The inner loop portion of the inner catheter control element or filament 19 will contract in diameter and pull on the inner circumference of the braided expansile loop 48 resulting in the central "hole" of the toroid becoming smaller and smaller in diameter 37. This results in the transverse diameter of the toroid becoming bigger while the outer diameter stays the same. Once the desired size is reached, the wire may be held in place and a polymeric or other biologically compatible material as describe above injected into the toroid either through the inner catheter control element which may be in the form of a hollow catheter or hypotube, or alternatively via a catheter which is advanced into the toroid along the inner catheter control element or filament 19 or separately using a catheter or needle for injection. The fully expanded expansile loop 48 can now be injected or filled with a suitable material for fusing the two adjacent vertebrae together. Candidates for a suitable fusing material include, but are not limited to, bond graft materials such as any described "bone cements" or any polymeric bone graft compounds, bone graft materials, nylon fibers, carbon fibers, glass fibers, collagen fibers, ceramic fibers, polyethylene fibers, poly(ethylene terephthalate), polyglycolides, polylactides, and combinations thereof.

Once the bone fusing material has been injected the inner catheter control element 19 may be removed by retracting it from the braided expansile loop. Alternatively, the inner catheter control element 19 may be cut off at its entrance point into the toroid. In another embodiment (not illustrated) the expansile loop may be expanded in diameter using an inner filament of sufficient stiffness such as the metal wire described and the central hole may be made smaller by pulling on a separate flexible filament such as a thread attached to the inner radius of the expansile braided.

In this embodiment of fusing two adjacent vertebrae together, it may be desirable to stimulate growth of bone through the fill material. To facilitate bone integration and growth, the expansile loop should have openings that are more porous. The pores or openings of the expansile loop will have a diameter of about 0.25 mm to about 5.0 mm. The size is selected to allow tissue in-growth while containing the material packed into the expansile loop. It is also contemplated that the expansile loop can be seeded in vitro with bone forming cells, such as osteoblasts, and/or with growth factors. Multiple layers of osteoblast-seeded applications may be stacked on top of one another and further allowed to or encouraged to proliferate. In addition to in vitro seeding of osteoblasts, other treatments for the braided expansile loop are contemplated that also provide an implant that allows for bone in-growth and regeneration of bony tissue. For example, the expansile loop can be coated with a demineralized bone matrix or smeared or coated with an osteoinductive bone paste, such as OSTEOFIL™. In addition, the expansile loop can be coated with collagen, and subsequently soaked in a pharmacological agent such as recombinant human bone morphogenic protein, antibiotic agents, or other similar material.

An additional feature that can be incorporated to all of the embodiments disclosed herein is the means for attaching or securing the expansile loop or mesh 59, 60, 61, 62 to the surrounding disc structures, the annulus 36 and/or the native or artificial nucleus 34 or the vertebral endplates 35. One benefit of the described invention is that the attachment means 64 can secure the circumferential expansile loop or mesh 59, 60, 61, 62 to healthy tissue located away from a damaged area or on the opposite side of the hernia or clinical entry site.

Figure 23:
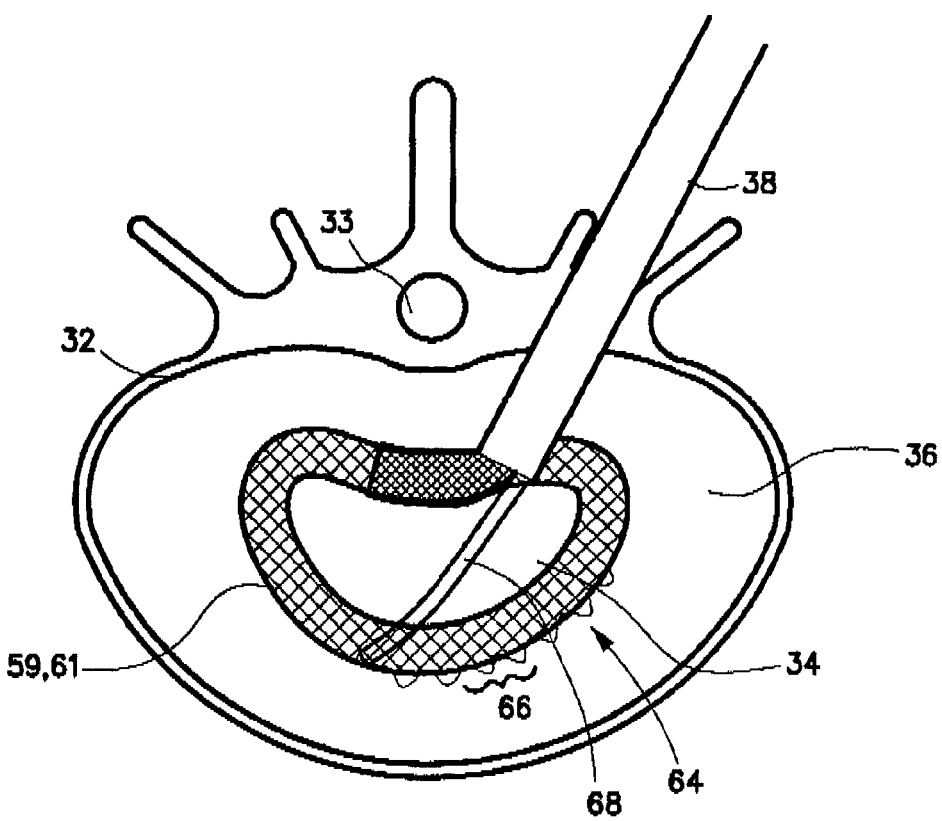
FIG. 23 is a cross sectional view of the attachment means in the from of a suture and demonstrating a suture delivery system already advanced through an access tube and utilizing non-absorbable or re-absorbable sutures to attach the contracted configuration of the expansile mesh to the inner wall of the annulus at multiple points.

Shown in FIG. 23 is a cross sectional view of the attachment means 64 in the from of a suture 66 and demonstrating a suture delivery system 68 already advanced through an access tube 38 and utilizing non-absorbable or re-absorbable sutures 66 to attach the contracted configuration of the expansile mesh 59, 61 to the inner wall of the annulus 36 at multiple points. Although not shown in FIG. 23, it is anticipated by the Applicants that the suture delivery system 68 can be used without the access tube 38 and can be advanced with or with the aid of endoscope through the access opening or potentially a hernia opening to perform the attachment procedure. Furthermore, other traditional surgical or manipulation techniques not utilizing a delivery system 68 can be used with or without the aid of an endoscope through the access opening or potentially a hernia opening to perform the attachment procedure.

The attachment means 64 for securing the expansile loop or mesh to the annulus 36 or native/artificial nucleus 34 could be through the use of previously known technology such as sutures, clips, tacks, anchors, staples, screws, buttons, T-shaped tags, barbed tags, adhesives or other similar devices having appropriate securing characteristics. The term "attachment means" used herein encompasses sutures, clips, tacks, anchors, staples, screws, clamps, buttons, T-shaped tags, barbed tags and other tissue holding means and delivery/manipulation techniques.

Whereby sutures 66 are known to be the standard in holding strength, the use of tacks, staples and other fasteners continue to be developed and implemented. Since the delivering, manipulating and retrieving a suture, often in a very tight surgical site is difficult the use and delivery of non-suture attachment means through a small opening to hold torn tissue have been shown to have a clinical advantage.

Figure 24:
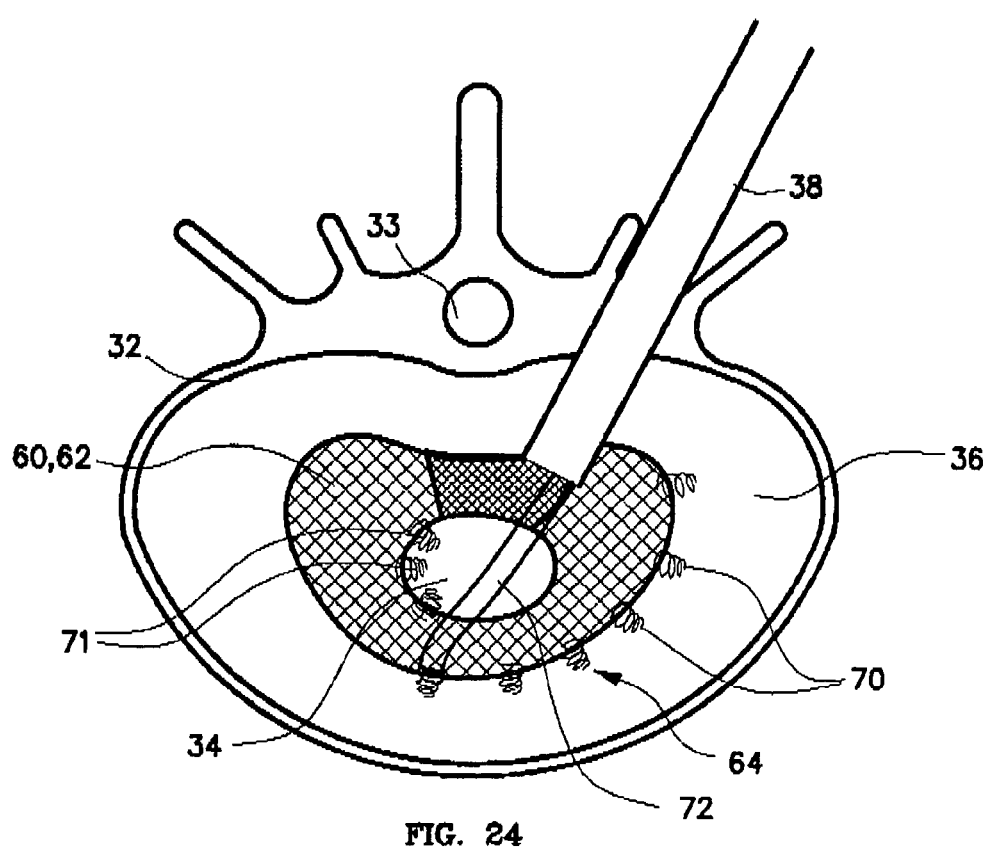
FIG. 24 shows a cross sectional view of the attachment means in the form of a staple or helicoil with a delivery system already advanced through the access tube and utilizing non-absorbable or re-absorbable stables or helicoil mechanism to secure the expanded expansile mesh to the inner wall of the annulus at multiple points. Also shown are non-absorbable or re-absorbable stables or helicoils used to attach the expanded expansile mesh to the outer wall of an artificial nucleus at multiple points.

FIG. 24 shows a cross sectional view of the attachment means 64 in the form of a staple or helicoil 70,71 with a delivery system 72 already advanced through the access tube 38 and utilizing non-absorbable or re-absorbable stables or helicoil mechanism 70 to secure the expanded expansile mesh 60, 62 to the inner wall of the annulus 36 at multiple points. The staple or helicoil is being provided as an example in this Figure since the attachment means 64 could be clips, tacks, anchors, staples, screws, clamps, buttons, T-shaped tags, barbed tags and other tissue holding means and delivery/manipulation techniques. Also shown in FIG. 24 is a cross sectional view of the a staple or helicoil delivery system 72 already advanced through the access tube 38 and utilizing non-absorbable or re-absorbable stables or helicoils 71 to attach the expanded expansile mesh 60, 62 to the outer wall of the native or artificial nucleus 34 at multiple points. Although not shown in FIG. 24, it is anticipated by the Applicants that the helicoil delivery system 72 can be used without the access tube 38 and can be advanced with or with the aid of an endoscope through the access opening or potentially a hernia opening to perform the attachment procedure. Furthermore, other traditional surgical or manipulation techniques not utilizing a delivery system 72 can be used with or without the aid of an endoscope through the access opening or potentially a hernia opening to perform the attachment procedure.

The attachment means 64 is designed to engage the outer surface of the expansile mesh and then engage the either the annulus 36 or the nucleus 34, securing the expansile loop or mesh in place. Besides securing the expansile mesh or loop in place, the use of an attachment means to secure the expansile mesh or loop can facilitate the in-growth of new tissues.

The annulus/nucleus attachment means 64 could be installed within the expansile mesh prior to insertion with the vertebral space. Alternately the annulus/nucleus attachment means 64 can be installed within the expansile mesh after is inserted into the disc in a contacting configuration or after the mesh is expanded in the disc. The annulus/nucleus attachment means 64 could be made from materials that are biodegradable or bioabsorbable such as resorbable collagen, LPLA (poly(l-lactide)), DLPLA (poly(dl-lactide)), LPLA-DLPLA, PGA (polyglycolide), PGA-LPLA or PGA-DLPLA, polylactic acid and polyglycolic acid which is broken down and bioabsorbed by the patient over a period of time.

Figure 25:
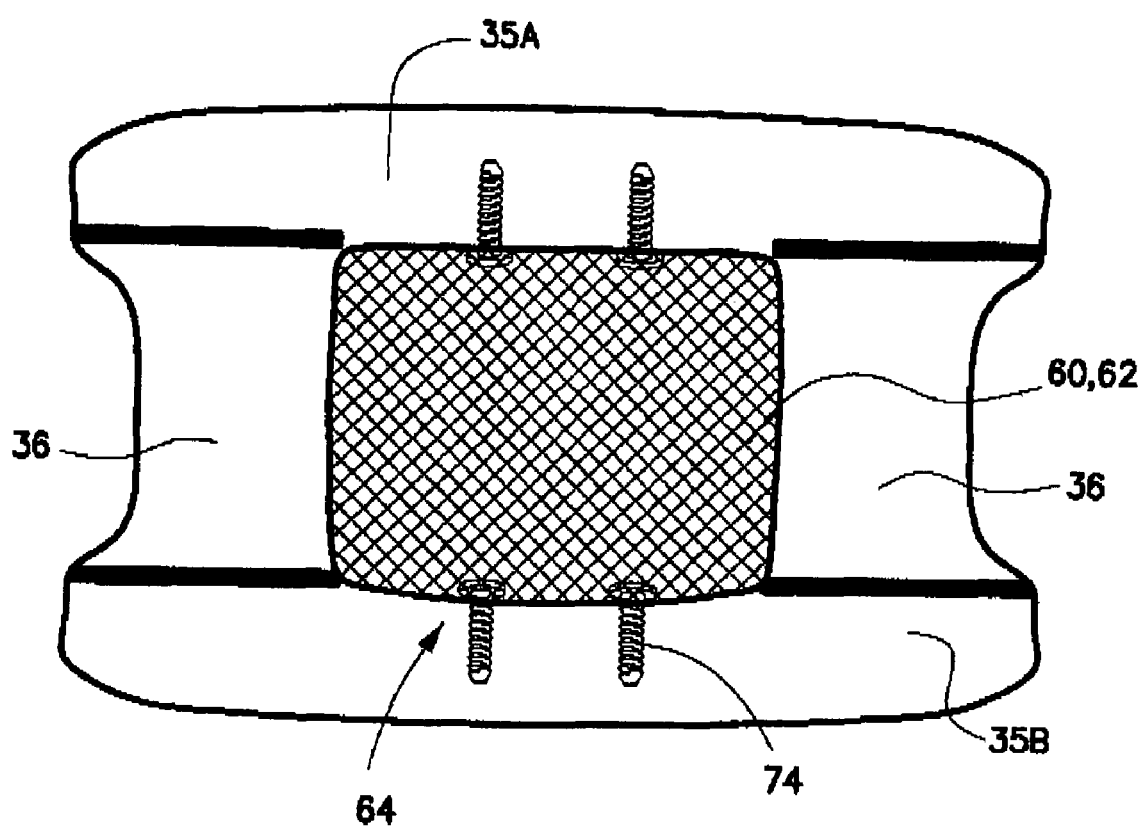
FIG. 25 shows a cross sectional view of the expansile mesh contained within a vertebral bone structure with the mesh attached to the bone structure by means of screws or anchors.

Furthermore, as shown in FIG. 25, the expansile loop or mesh 60, 62 could be expanded and secured to an endplate 35a or 35b or both endplates 35a and 35b of the vertebral body. Also shown is annular tissue 36 sandwiched between the two vertebral endplates 35. Such attachments means 64 are the same as the annulus 36 means but are designed for placement into hard bony tissues. This includes bone screws, anchors, and other means 74 for attachment to hard tissue.

Attachment to the native nucleus could be required if a partial nuclectomy is performed. Attachment to an artificial nucleus 34 could be performed following nuclectomy and placement of an artificial nucleus. Attachment of expansile mesh 60, 62 to the artificial nucleus 34 could stabilize the artificial nucleus and/or maintain the artificial nucleus's position during delivery, during mesh expansion and over time.

Attachment of the expansile mesh 60, 62 to the annulus 36, native or artificial nucleus 34, or the endplates 35 could encourage in-growth of body tissues throughout the expansile mesh 60, 62 and therefore function to reinforce and repair the annulus and strengthen the annulus or nucleus. Overall, the placement of the attachment means 64 into healthy tissue will increase long-term stability.

One significant advantage of the described invention and attachment means is that the attachment means may be placed into healthy annular tissue located distal to the annulectomy site or site of hernia defect. This is due to the complete circumferential nature of the expansile loop within the inner surface of the annulus. This is an advantage over previously described systems used to patch a hole created in the annulus in the area of a hernia defect or diseased tissue.

In addition, the expansile mesh 59, 60, 61, 62, can include materials that will act as a scaffold or carrier for delivering biologic medicaments to vertebral tissues. The expansile mesh can be previously treated (for example, by soaking) with certain biologics (e.g. BMP, OP-1), or the access tube can be constructed to include a biologic delivery means such that the biologic is 1) delivered while the attachment means 64 is being deployed, 2) delivered prior to deploying the attachment means 64, 3) delivery subsequent to deploying the attachment means 64, or any combinations thereof.

It should be understood that the foregoing description of the present invention is intended merely to be illustrative thereof and that other embodiments, modifications, and equivalents of the invention are within the scope of the invention recited in the claims appended hereto. Further, although each embodiment described above includes certain features, the invention is not limited in this respect. Thus, one or more of the above-described or other features of the invention, method of delivery, or injection of biomaterial may be employed singularly or in any suitable combination, as the present invention is not limited to a specific embodiment.

The invention claimed is:

1. A method for artificial disc replacement comprising the steps of:

incorporating an attachment means within a flexible and expandable expansile mesh, said expansile mesh having a control element and is held in a contracted configuration;

positioning said expansile mesh within an intervertebral space of a patient or animal;

expanding said expansile mesh without pressurization, within said intervertebral space in a substantially circumferential manner against the inner annular wall by use of the control element acting directly on the mesh, the expanded expansile mesh having a substantially continuous mesh loop configuration that surrounds a disc nucleus;

activating said attachment means whereby said attachment means substantially engages said expansile mesh to artificial or natural vertebral tissues.

2. The method of claim 1 wherein said attachment means comprises one or more staples.

3. The method of claim 1 wherein said attachment means comprises one or more sutures.

4. The method of claim 1 wherein said attachment means comprises one or more helicoils.

5. The method of claim 1 wherein said attachment means comprises one or more T-shaped clips or barbed T-shaped clips.

6. The method of claim 1 wherein said vertebral tissues is one or more endplates of the vertebrae.

7. The method of claim 6 wherein said attachment means comprises one or more screws.

8. The method of claim 1 wherein said vertebral tissues are native.

9. The method of claim 1 wherein said vertebral tissues are substantially native nucleus.

10. The method of claim 1 wherein said vertebral tissues are substantially artificial nucleus.

11. The method of claim 1 wherein said vertebral tissues are healthy tissues.

12. The method of claim 1 wherein said attachment means is re-absorbable or biodegradable.

13. The method of claim 1, further comprising the step of delivering a biologic medicament from said expansile mesh while said attachment means is being deployed.

14. The method of claim 1, further comprising the step of delivering a biologic medicament from said expansile mesh prior to deploying said attachment means.

15. The method of claim 1, further comprising the step of delivering a biologic medicament from said expansile mesh subsequent to deployment of said attachment means.

16. The method of claim 1, further comprising the step of delivering a biologic medicament from said expansile mesh over time after the surgical procedure.

17. The method of claim 1, further comprising the step of delivering a biologic medicament from an access opening while said attachment means is being deployed.

18. The method of claim 1, further comprising the step of delivering a biologic medicament from an access opening prior to deploying said attachment means.

19. The method of claim 1, further comprising the step of delivering a biologic medicament from an access opening subsequent to deployment of said attachment means.

20. A method for artificial disc replacement comprising the steps of:
providing a flexible and expandable expansile mesh having a control element;
positioning said expansile mesh while said mesh is in a contracted configuration within an intervertebral space of a patient or animal;
incorporating an attachment means within said flexible and expandable expansile mesh;
expanding said expansile mesh without pressurization within said intervertebral space in a substantially circumferential manner against the inner annular wall by use of the control element acting directly on the mesh, the expanded mesh having a substantially continuous mesh loop configuration that surrounds a disc nucleus;
activating said attachment means whereby said attachment means substantially engages said expansile mesh to artificial or natural vertebral tissues.

21. The method of claim 20 wherein said attachment means comprises one or more staples.

22. The method of claim 20 wherein said attachment means comprises one or more sutures.

23. The method of claim 20 wherein said attachment means comprises one or more helicoils.

24. The method of claim 20 wherein said attachment means comprises one or more T-shaped clips or barbed T-shaped clips.

25. The method of claim 20 wherein said vertebral tissues is one or more endplates of the vertebrae.

26. The method of claim 25 wherein said attachment means comprises one or more screws.

27. The method of claim 1 wherein said vertebral tissues are native.

28. The method of claim 20 wherein said vertebral tissues are substantially native nucleus.

29. The method of claim 20 wherein said vertebral tissues are substantially artificial nucleus.

30. The method of claim 20 wherein said vertebral tissues are healthy tissues.

31. The method of claim 20 wherein said attachment means is re-absorbable or biodegradable.

32. The method of claim 20, further comprising the step of delivering a biologic medicament from said expansile mesh while said attachment means is being deployed.

33. The method of claim 20, further comprising the step of delivering a biologic medicament from said expansile mesh prior to deploying said attachment means.

34. The method of claim 20, further comprising the step of delivering a biologic medicament from said expansile mesh subsequent to deployment of said attachment means.

35. The method of claim 20, further comprising the step of delivering a biologic medicament from an access opening while said attachment means is being deployed.

36. The method of claim 20, further comprising the step of delivering a biologic medicament from an access opening prior to deploying said attachment means.

37. The method of claim 20, further comprising the step of delivering a biologic medicament from an access opening subsequent to deployment of said attachment means.

38. The method of claim 20, further comprising the step of delivering a biologic medicament from said expansile mesh over time after the surgical procedure.

39. A method for artificial disc replacement comprising the steps of:
providing an expansile mesh having a control element;
positioning said expansile mesh while said mesh is in a contracted configuration within an intervertebral space of a patient or animal;
expanding said expansile mesh without pressurization within said intervertebral space in a substantially circumferential manner against the inner annular wall by use of the control element acting directly on the mesh, the expanded mesh having a substantially continuous mesh loop configuration that surrounds a disc nucleus;
incorporating an attachment means within the expanded expansile mesh;
activating said attachment means whereby said attachment means substantially engages said expansile mesh to artificial or natural vertebral tissues.

40. The method of claim 39 wherein said attachment means comprises one or more staples.

41. The method of claim 39 wherein said attachment means comprises one or more sutures.

42. The method of claim 39 wherein said attachment means comprises one or more helicoils.

43. The method of claim 39 wherein said attachment means comprises one or more T-shaped clips or barbed T-shaped clips.

44. The method of claim 39 wherein said vertebral tissues is one or more endplates of the vertebrae.

45. The method of claim 44 wherein said attachment means comprises one or more screws.

46. The method of claim 1 wherein said vertebral tissues are native.

47. The method of claim 39 wherein said vertebral tissues are substantially native nucleus.

48. The method of claim 39 wherein said vertebral tissues are substantially artificial nucleus.

49. The method of claim 39 wherein said vertebral tissues are healthy tissues.

50. The method of claim 39 wherein said attachment means is re-absorbable or biodegradable.

51. The method of claim 39, further comprising the step of delivering a biologic medicament from said expansile mesh while said attachment means is being deployed.

52. The method of claim 39, further comprising the step of delivering a biologic medicament from said expansile mesh prior to deploying said attachment means.

53. The method of claim 39, further comprising the step of delivering a biologic medicament from said expansile mesh subsequent to deployment of said attachment means.

54. The method of claim 39, further comprising the step of delivering a biologic medicament from an access opening while said attachment means is being deployed.

55. The method of claim 39, further comprising the step of delivering a biologic medicament from an access opening prior to deploying said attachment means.

56. The method of claim 39, further comprising the step of delivering a biologic medicament from an access opening subsequent to deployment of said attachment means.

57. The method of claim 39, further comprising the step of delivering a biologic medicament from said expansile mesh over time after the surgical procedure.

* * * * *